(12) United States Patent
Basheer

(10) Patent No.: US 6,605,452 B1
(45) Date of Patent: Aug. 12, 2003

(54) FATTY ACID POLYOL ESTER-COATED LIPASE COMPLEX IMMOBILIZED ON INSOLUBLE MATRIX

(75) Inventor: Sobhi Basheer, Sakhnine (IL)

(73) Assignee: Enzymotec, Ltd., Nazareth Illit (IL)

( * ) Notice: Subject to any disclaimer, the term of this patent is extended or adjusted under 35 U.S.C. 154(b) by 0 days.

(21) Appl. No.: 09/274,545

(22) Filed: Mar. 23, 1999

Related U.S. Application Data

(63) Continuation-in-part of application No. PCT/US98/15799, filed on Jul. 28, 1998, and a continuation-in-part of application No. 08/936,690, filed on Sep. 24, 1997, now abandoned.

(51) Int. Cl.[7] .............................. C12P 7/64; C12P 7/62; C12N 11/04; C12N 11/02; C12N 9/20
(52) U.S. Cl. ...................... 435/134; 435/135; 435/159; 435/176; 435/177; 435/180; 435/198
(58) Field of Search .................. 435/134, 135, 435/159, 176, 177, 180, 198

(56) References Cited

U.S. PATENT DOCUMENTS

| | | | |
|---|---|---|---|
| 5,342,768 A | * | 8/1994 | Pederson et al. ........... 435/134 |
| 5,773,266 A | * | 6/1998 | Bosley et al. ............... 435/176 |

OTHER PUBLICATIONS

Basheer, et al., Biotech, and Bioengineering, 45:187–195, (1995).*
Goto et al., Biotech, and Bioengineering, 45:27–32, (1995).*
Bashneer, et al., Process Biochemistry, 30 : 531–536, (1995).*

* cited by examiner

*Primary Examiner*—David M. Naff
(74) *Attorney, Agent, or Firm*—Banner & Witcoff, Ltd.

(57) ABSTRACT

A lipase preparation is prepared containing a surfactant-coated lipase complex immobilized onto an insoluble matrix. A preferred surfactant is a fatty acid polyol ester such as sorbitan monostearate (SMS). The lipase preparation may be provided in granulated form or in an organic solvent, and can be used in esterifying, inter-esterifying, trans-esterifying and alcoholysing reactions with no added water. The lipase preferably has 1,3-positional specificity with respect to triacylglycerols, and the insoluble matrix may be modified with a fatty acid derivative. A lipase in aqueous medium is contacted with a surfactant to coat the lipase with the surfactant, and the coated lipase is immobilized onto an insoluble matrix to produce the lipase preparation which may be dried such as by freeze drying. Alternatively, the lipase may be first contacted with the insoluble matrix, and thereafter with the surfactant.

52 Claims, 8 Drawing Sheets

Acidolysis reaction:

Transesterification reaction:

1

FATTY ACID POLYOL ESTER-COATED LIPASE COMPLEX IMMOBILIZED ON INSOLUBLE MATRIX

This application is a continuation-in-part of application Ser. No. 08/936,690, filed Sep. 24, 1997, now abandoned, and of PCT/US98/15799, filed Jul. 28, 1998.

FIELD OF THE INVENTION

The present invention relates to an insoluble matrix immobilized surfactant-coated lipase complex, to a method of preparing same and to the use of same as a biocatalyst for catalyzing, for example, inter- and/or trans-esterification of oils and fats in hydrophobic organic media. The novel procedures include two steps. In the first step, the enzyme is activated by being coated with a surfactant. In the second step, the enzyme is immobilized on the matrix of choice. These steps can be executed in any order.

BACKGROUND OF THE INVENTION

Enzymatic modification of the structure and composition of oils and fats is of great industrial and clinical interest. This process is accomplished by exploiting regio-specific lipases in inter-esterification and/or trans-esterification reactions utilizing fats or oils as substrates (Macrea, A. R., 1983, J. Am. Oil Chem. Soc. 60: 291–294).

Using an enzymatic process, it is possible to incorporate a desired fatty acyl group on a specific position of a triacylglycerol molecule, whereas conventional chemical inter-esterification does not possess regio-specificity. Conventionally, chemical reactions are promoted by sodium metal, sodium alkoxide or cobalt chloride that catalyze acyl migration among triglyceride molecules, leading to the production of triglycenrdes possessing randomly distributed fatty acyl residues (Erdem-Senatalar, A., Erencek, E. and Erciyes, A. T., 1995, J. Am. Oil Chem. Soc. 72: 891–894).

In recent years, a number of studies have demonstrated the potential application of lipases as promising biocatalysts for different esterification reactions in organic media (Wisdom, R. A., Dunhill, P., and Lilly, M. D., 1987, Biotechnol. Bioeng. 29: 1081–1085).

Lipases with 1,3-positional specificity principally catalyze hydrolysis of fats and oils, to yield free fatty acids and glycerol. However, recent studies have shown that lipases with 1,3-positional specificity are also capable of catalyzing two types of esterification reaction in microaqueous organic media (Quinlan, P. & Moore, S., 1993, INFORM 4: 580–585). The first of these reactions is an inter-esterification or acidolysis reaction in which free fatty acids react with different triglycerides to yield new triglyceride molecules. The second type of reaction is trans-esterification in which two different triglyceride molecules react to give new triglyceride molecules (see FIGS. 1a–b). In both of these enzymatic reactions, the sn-2 position of the reacting triglycerides remains unchanged.

In general, water concentration plays an important role in determining the activity of enzymes. It also affects the equilibrium state of the reactions performed in hydrophobic organic solvents (Valiverty, R. H., Halling, P. J. and Macrae, A. R., 1993, Biotechnol. Lett. 15: 1133–1138). Since water is vital for the activity of enzymes in both hydrolysis as well as in synthesis reactions, as a compromise between hydrolysis and synthesis of triglycerides, the concentration of water is lowered so that the occurrence of undesirable reactions is minimized, but the water available is sufficient for the enzyme to remain active.

At high concentrations of water, e.g., above 5% of solvent weight, lipases possess preferably their natural hydrolytic activity, therefore, hydrolysis reaction proceeds. However, at low concentrations of water, e.g., below 1% of solvent weight, lipases catalyze the reverse reaction, that is, synthesis.

A typical range of water concentrations needed for promotion of inter-esterification reaction between different oils in organic media is 1–10 weight percent (wt %) of the hydrophobic organic solvent. This water concentration can normally facilitate also the hydrolysis reaction thus producing undesirable partial glycerides (mono- and di-glycerides) in the range of 10–20 wt % of the initial triglycerides concentration, as by products The scope for exploiting the positional specificity of lipases, especially, in the food and oleochemical industries for the production of high-valued special fats is enormous. For example, cocoa butter substitute, simulated human milk fat and other structured triglyceride of specific nutritional quality can be obtained enzymatically by employing lipases with 1,3-positional specificity (Vulfson, E. N., 1998, Trends Food Sci. Technol 4.209–215)

In view of the foregoing, it is recognized that there is a need to develop new structured triglycerides with both medium-chain and -3 polyunsaturated fatty acids that would be devoid of the adverse effects of the naturally occurring -3 polyunsaturated fatty acids, or saturated fatty acids. For example, molecules of MCTs having one of their acyl groups substituted with an essential long-chain fatty acid would provide the nutritional advantages of both MCTs and LCTs. This approach is illustrated by the very useful triglyceride that is formed by incorporating the acyl form of the polyunsaturated fatty acids, EPA, DHA or -linolenic acid at the Sn-2 position of a triglyceride molecule having a medium-chain fatty acyl group at the sn-1 and sn-3 positions (Odle, J., 1997, J. Nut. 127: 1061).

The aforementioned polyunsaturated fatty acids incorporated into triglyceride molecules were shown to have several health benefits with respect to cardiovascular disease, immune disorders and inflammation, allergies, diabetes, kidney diseases, depression, brain development and cancer. Furthermore, medium-chain fatty acids incorporated into the same triglyceride molecule are of major importance in some clinical uses, especially, for facilitating absorbability and solubilization of cholesterol in blood serum, and for providing readily available energy sources for body consumption.

Many different approaches for the use of lipases in organic media have been attempted in order to activate them and to improve their performance.

These include the use of lipase powder suspended in either microaqueous organic solvents or in biphasic systems, and native lipases is adsorbed on microporous matrices in fixed- and fluidized-bed reactors (Malcata, et al., 1990, J. Am. Oil Chem. Soc. 890–910). Furthermore, lipases have been hosted in reverse micelles, and in some studies lipases were attached to polyethylene glycol or hydrophobic residues to increase their solubility and dispersibility in organic solvents.

None of the abovementioned approaches was found to be applicable for all enzymatic systems. However, in many cases, when lipases were treated in one way or another as described, their performance with respect to activity, specificity, stability and dispersibility in hydrophobic organic systems was improved.

In recent studies, the development of surfactant-coated lipase preparations has been reported (e.g., Basheer, S., Mogi, K. and Nakajima, M., 1995, Biotechnol. Bioeng. 45: 187–195). This enzyme modification converts slightly active or completely inactive lipases, with respect to esterification of triglycerides and fatty acids in organic media, into highly active biocatalysts. The newly developed surfactant-lipase complexes have been further studied and used for the inter-esterification reaction in organic solvent systems to produce structured triglycerides of major importance in medical applications (Tanaka, Y., Hirano, J. and Funada, T., 1994, J. Am. Oil Chem. Soc. 71: 331–834).

In another approach to the problem, various immobilized-enzyme reactor systems were used in lipase-catalyzed reactions in microaqueous hydrophobic organic media (e.g., Basheer, S., Mogi, K., Nakajima, M., 1995, Process. Biochemistry 30: 531–536). These included fixed- and fluidized-bed reactors, and a slurry reactor. In the published studies, lipase immobilized onto an inorganic matrix was used both in a batch reactor system, and in fixed-bed bioreactor systems. However, the lipases employed were not surfactant-coated and therefore have the same limitations as free lipase systems. These limitations include:

1. Difficulties in recovering the enzyme after completion of the process;
2. Rapid loss of activity of the free enzyme in the reaction medium;
3. Problems of recoverabilty of expensive enzymes;
4. Low synthetic activity of free lipases in organic solvents.

Neither of the abovementioned strategies has satisfactorily solved the technical problems encountered in directing trans- and inter-esterification of fats and oils. It is therefore an object of the invention to provide a lipase preparation that is capable of catalyzing esterification reactions in fats and oils with a much greater efficacy than existing methods.

It is another purpose of the invention to provide a lipase preparation that incorporates both immobilization to a matrix, and treatment by coating with a surfactant.

It is a further object of the invention to provide such a lipase preparation that may be used repeatedly, on an industrial scale with minimal loss of activity.

It is a further object of the invention to provide a method for preparing said insoluble matrix-immobilized, surfactant-coated lipase complex.

Yet a further purpose of the invention is to provide a process for preparing structured triacylglycerols, using said insoluble matrix-immobilized, surfactant-coated lipase complexes.

Other objects and advantages of the invention will become apparent as the description proceeds.

SUMMARY OF THE INVENTION

It has now been surprisingly found, and this is an object of the invention, that the dual modification of crude lipase by (1) coating with a surfactant, and (2) immobilization to an insoluble matrix; results in a synergistic improvement in the efficiency of the enzyme to catalyze trans- and inter-esterification reactions, when compared to either of these two treatments alone. It has been further unexpectedly found that it is possible to enhance the catalytic stability of said dually modified lipase for esterification reactions, by providing the enzyme preparation in a granulated form.

The invention is primarily directed to a lipase preparation comprising an insoluble matrix and a surfactant-coated lipase complex immobilized onto said insoluble matrix.

The immobilization of the lipase complex onto the insoluble matrix may be achieved by several different methods. According to a preferred embodiment of the invention, however, the surfactant-coated lipase complex is covalently, ionically or physically bound to the insoluble matrix.

The invention encompasses the use of many types of matrix, said matrices being selected from the group consisting of an inorganic insoluble matrix and an organic insoluble matrix.

In a preferred embodiment of the invention, the inorganic insoluble matrix is selected from the group consisting of alumina, diatomaceous earth, Celite, calcium carbonate, calcium sulfate, ion-exchange resin, silica gel and charcoal.

The abovementioned ion-exchange resin may be of any suitable material, but in a preferred embodiment is selected from the group consisting of Amberlite and Dowex.

Although any suitable organic insoluble matrix may be use, in a preferred embodiment of the invention, the organic insoluble matrix is selected from the group consisting of Eupergit, ethylsulfoxycellulose and aluminium stearate.

In a preferred embodiment, the content of the lipase is 2–20 weight percent of the surfactant-coated lipase complex. In a still more preferred embodiment, the content of the lipase is 0.01–1.0 weight percent of the preparation.

The invention provides the above-described lipase preparation, wherein the surfactant in the surfactant-coated lipase complex includes a fatty acid conjugated to a hydrophilic moiety. In a preferred embodiment, the fatty acid is selected from the group consisting of monolaurate, monomyristate, monopalmitate, monostearate, dilaurate, dimyristate, dipalmitate, distearate, trilaurate, trimyristate, tripalmitate and tristearate. In a preferred embodiment, the hydrophilic moiety is selected from the group consisting of a sugar, a phosphate group, a carboxylic group and a hydroxylated organic residue. In a more preferred embodiment, the sugar is selected from the group consisting of sorbitol, sucrose, glucose and lactose. Although the fatty acid and the hydrophilic moiety may be linked by any suitable type of bond, in a preferred embodiment, the fatty acid and the hydrophilic moiety are conjugated via an ester bond.

Although the lipase may be derived or obtained from any convenient source, in a preferred embodiment, the lipase is derived from a microorganism. Many different species of both microorganisms and multicellular organisms may be used as a source of lipase for the lipase preparation of the invention. The invention, however, is particularly directed to the use of lipase that is derived from a species selected from the group consisting of Burkholderia sp., *Candida antractica B, Candida rugosa*, Pseudomnonas sp., *Candida antractica A*, Porcine pancreas lipase, Humicola sp., *Mucor miehei, Rhizopus javan., Pseudomonas fluor., Candida cylindrcae, Aspergillus niger, Rhizopus oryzae, Mucor jaanicus*, Rhizopus sp., *Rhizopus japonicus and Candida antractica*.

In a further aspect, the invention is directed to a lipase preparation comprising an insoluble matrix and a surfactant-coated lipase complex immobilized onto said insoluble matrix, said lipase preparation being provided in an organic solvent. In a preferred embodiment, the organic solvent is selected from the group consisting of n-hexane, toluene, iso-octane, n-octane, benzene, cyclohexane and di-iso-propylether. The invention is further directed to the use of said lipase preparation as a catalyst for esterification, inter-esterification and trans-esterification of oils and fats and alcoholysis of triglycerols and fatty alcohols. In a preferred embodiment, the lipase preparation is used as a catalyst with 1,3-positional specificity with respect to triacylglycerols.

In another aspect, the invention is directed to a lipase preparation as described above, wherein said preparation is in granulated form.

The invention also provides a lipase preparation, as described hereinabove, wherein the insoluble matrix has been modified with a fatty acid derivative.

In a further aspect the invention is directed to an enzyme preparation, as described hereinabove, for use in a reaction environment without the need for water addition.

The invention also encompasses a method for improving the stability of a surfactant-coated immobilized lipase complex, comprising granulating same prior to contacting it with the substrate to be reacted.

In a further aspect, the invention provides a method of preparing an insoluble matrix-immobilized surfactant-coated lipase complex comprising, in any desired order, the steps of:

(a) contacting a lipase in an aqueous medium with a surfactant, at a concentration and temperature, and for a period of time sufficient to obtain a coating of said lipase; and (b) contacting said lipase in an aqueous medium, with an insoluble matrix, at a concentration, under conditions and for a period of time sufficient to obtain immobilization of said lipase on said matrix.

In a preferred embodiment of the abovementioned method, the lipase is first contacted with the insoluble matrix, and thereafter with the surfactant. In another preferred embodiment thereof, the lipase is first contacted with the surfactant, and thereafter with the insoluble matrix.

In a preferred embodiment of the invention, the above-described method further comprises the separation of the matrix-immobilized surfactant-coated lipase complex from the aqueous solution in which it was formed. In a still more preferred embodiment, this method also further comprises the step of drying said matrix-immobilized surfactant-coated lipase complex. Although the drying step may be accomplished by any convenient method, in a preferred embodiment, said drying is effected by freeze drying. In another preferred embodiment, the matrix-immobilized surfactant-coated lipase complex is dried to a water content of less than 100 parts per million by weight.

In another preferred embodiment, the aqueous solution used in the above-described method is a buffered-aqueous solution.

In yet another preferred embodiment of the above-described method, the lipase and surfactant are contacted in the aqueous medium by:

(i) dissolving said surfactant in an organic solvent for obtaining a dissolved surfactant solution; and (ii) mixing said lipase and said dissolved surfactant solution in said aqueous medium.

In another preferred embodiment, the method further comprises sonication of the aqueous solution.

In yet another preferred embodiment of the method of the invention, the insoluble matrix is selected from the group consisting of alumina, diatomaceous earth, Celite, calcium carbonate, calcium sulfate, ion-exchange resin, silica gel, charcoal, Eupergit, ethylsulfoxycellulose, aluminium stearate and fatty acid derivative-treated Celite or other inorganic matrices.

In another preferred embodiment, the surfactant of the method includes a fatty acid conjugated to a hydrophilic moiety. In a still more preferred embodiment, said fatty acid is selected from the group consisting of monolaurate, monomyristate, monopalmitate, monostearate, dilaurate, dimyristate, dipalmitate, distearate, trilaurate, trimyristate, tripalmitate and tristearate.

In another preferred embodiment of the method of the invention, the hydrophilic moiety is selected from the group consisting of a sugar and a phosphate group and a carboxylic group and a polyhydroxylated organic residue. In a still more preferred embodiment, the sugar is selected from the group consisting of sorbitol, sucrose, glucose and lactose.

In another preferred embodiment of the method of the invention, the fatty acid and the hydrophilic moiety are conjugated via an eater bond.

In a preferred embodiment of the method of the invention, the lipase is derived from an organism. In a more preferred embodiment, the lipase is derived from a multicellular microorganism. Although the lipase may be derived from any suitable host, in a preferred embodiment, the lipase is derived from a species selected from the group consisting of Burkholderia sp., *Candida antarctica B*, *Candida rugosa*, Pseudomnonas sp., *Candida antractica A*, *Porcine pancreatic lipase*, Humicola sp., *Mucor miehei*, *Rhizopus javan.*, *Pseudomnonas flour.*, *Candida cylindrcae*, *Aspergillus niger*, *Rhizopus oryzae*, *Mucor jauanicus*, Rhizopus sp., *Rhizopus japonicus* and *Candida antarctica*.

In another aspect, the invention is directed to a process for preparing structured triacylglycerols by esterification, acidolysis, trans-esterification, inter-esterification or alcoholysis between two substrates comprising contacting an insoluble matrix-immobilized surfactant-coated lipase complex with said substrates.

In a preferred embodiment of this process, the matrix-immobilized surfactant-coated lipase complex is contacted with the substrates in the presence of an organic solvent.

In another preferred embodiment of this process, at least one of the substrates is selected from the group consisting of an oil, a fatty acid, a triacylglycerol and a fatty alcohol. Although many different types of oil may be used in this process, in a preferred embodiment, the oil is selected from the group consisting of olive oil, soybean oil, peanut oil, fish oil, palm oil, cotton seeds oil, sunflower oil, Nigella sativa oil, canola oil and corn oil.

In another preferred embodiment, the fatty acid is selected from the group consisting of medium and short-chain fatty acids and their ester derivatives. In a still more preferred embodiment, the fatty acid is selected from the group consisting of oleic acid, palmitic acid, linolic acid, linolenic acid, stearic acid, arachidonic acid, eicosapentaenoic acid, docosahexaenoic acid and their ester derivatives.

While the above-described process may be performed in any suitable receptacle, said process, in a preferred embodiment, is carried out in a tank reactor or in a fixed-bed reactor.

The invention also encompasses a triacylglycerol prepared according to the above-described process for use as a cocoa butter substitute, human milk fat-like triglycerides for special diets, or structured triglycerides for medical applications.

BRIEF DESCRIPTION OF THE DRAWINGS

The invention herein described, by way of example only, with reference to the accompanying drawings, wherein.

DETAILED DESCRIPTION OF PREFERRED EMBODIMENTS

Figure 1A:
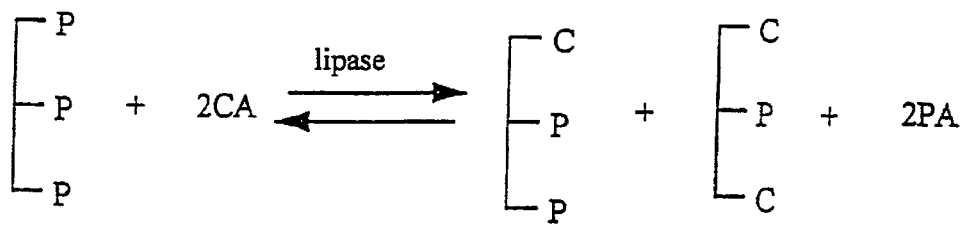
FIG. 1a presents an inter-esterification acidolysis reaction catalyzed by lipase with 1,3-positional specificity. P represents glycerol bound palmitic acid, C represents glycerol bound capric acid. PA and CA represent free palmitic and capric acids, respectively.
Figure 1B:
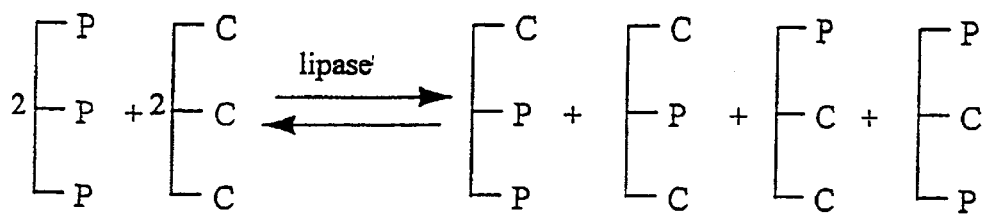
FIG. 1b presents a trans-esterification reaction catalyzed by lipase with 1,3-positional specificity. P represents glycerol bound palmitic acid and C represents glycerol bound capric acid.

The present invention relates to a surfactant-coated lipase or phospholipase complex immobilized on an organic or inorganic insoluble matrix (e.g., particulate solid support) which can be used to catalyze inter and trans-esterification reactions, particularly of oils and fats and alcoholysis of fatty-alcohols. The invention also makes provision for preparing the enzyme preparation in a granulated form that demonstrates increased stability of activity. Specifically, the present invention can be used for preparing structured triacylglycerols possessing desired nutritional or biochemical properties. The present invention is further directed to a method of preparing an insoluble matrix-immobilized surfactant-coated lipase or phospholipase complex and of a process of modifying oils and fats using an insoluble matrix-immobilized surfactant-coated lipase or phospholipase complex.

The principles and operation of the present invention may be better understood with reference to the drawings and accompanying descriptions.

It is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to the present invention surfactant-coated lipases or phospholipases are immobilized onto insoluble matrices by three different methods: (i) immobilization through hydrophobic (physical) adsorption on inorganic or organic insoluble matrices; (ii) immobilization through ionic interactions on various ion exchange resins (polar or apolar matrices); and (iii) immobilization through covalent immobilization to insoluble matrix such as Eupergit (organic matrix).

The immobilized surfactant-coated lipases prepared according to the procedures described herein were used to catalyze inter-esterification reactions between triglycerides and fatty acids, one-step alcoholysis reactions between triglycerides and fatty alcohols for production of wax esters, and also trans-esterification reactions between two different triglyceride molecules or between two different oils.

The results indicate that coating lipases with a lipid surfactant, such as, but not limited to, fatty acid sugar ester types, lead to activation of the lipases for use in organic synthesis and in most cases the modification process converts relatively inactive crude lipases to highly active biocatalysts. To develop an efficient enzymatic inter/trans-esterification bioreactor from which the lipase enzyme can be easily recovered or used continuously, surfactant-lipase complexes immobilized on organic and inorganic matrices, were used.

It was found that surfactant-coated lipases immobilized on an organic or inorganic matrix showed high inter/trans-esterification activity and only slight activity losses in five consecutive inter-esterification runs using the same biocatalyst batch. It was further found that granulation of the matrix-bound, surfactant-treated enzyme considerably enhanced the stability of the enzyme, permitting its repeated use without substantial loss of activity.

The immobilized surfactant-lipase complexes prepared according to the present invention were used for the preparation of structured triglycerides which have potential applications in medicine and the food industry. The triglycerides of interest that were synthesized according to the method of the present invention were produced by inter-esterification of long-chain triglycerides, such as the hard fraction of palm oil, with short-chain fatty acids such as capric acid. Immobilized surfactant-coated lipase catalyzed reactions yielded predominantly products with 1,3-positional specificity for the triglycerides of interest. Mono- and di-glycerides were also produced in a hydrolysis side reaction and their percentage was typically less than 7 weight percent of the initial triglyceride concentration. The operational stability of surfactant-lipase complexes immobilized on different solid matrices was very high, particularly following the optional granulation step, and no significant enzyme activity losses were observed.

Inter-esterification reactions using the immobilized surfactant-lipase complexes were also carried out to obtain fats of special characteristics with regard to their physical properties. For example, liquid olive oil was trans-esterified with the hard fraction of palm olein in order to obtain blends of oil for preparation of healthier olive oil based margarines. This enzymatic process is a useful alternative for chemical oil hydrogenation or interesterification processes.

Thus, in accordance with the teachings of the present invention there is provided a lipase preparation which includes an insoluble matrix and a surfactant-coated lipase complex immobilized onto the insoluble matrix.

As used herein in the specification and in the claims section below the term "lipase" is not limited to this specific enzyme, but is meant to embrace also similar enzymes such as phospholipase, proteases and glycosidaes. Other suitable enzymes will be readily apparent to the skilled chemist, and are therefore not listed herein, for the sake of brevity.

According to a preferred embodiment the complex is immobilized to the insoluble matrix via hydrophobic (physical) interaction, ionic interaction or via covalent immobilization.

In a preferred embodiment of the invention the insoluble matrix is an inorganic insoluble matrix, the term "insoluble" referring to its lack of solubility in both polar (e.g., water) and non-polar (hydrophobic) solvents. Preferably, the inorganic insoluble matrix according to the present invention is alumina, aluminium stearate, Celite, calcium carbonate, silica gel, charcoal, calcium sulfate, ion-exchange resin, such as, but not limited to, Amberlite and Dowex. For physical immobilization, most preferably the inorganic insoluble matrix employed is diatomaceous earth (DE). For ionic immobilization most preferably the inorganic insoluble matrix employed is Amberlite and Dowex, which are strong ion exchangers.

Suitable organic solid matrices according to the present invention include Eupergit for covalent immobilization and ethylsolfoxycellulose for ion interaction. Any other suitable organic solid matrix may also be used without exceeding the scope of the invention.

In another preferred embodiment of the present invention the lipase represents 2–20, preferably 5–11, weight percent of the surfactant-coated lipase complex. In yet another preferred embodiment of the present invention the lipase represents 0.01–1 weight percent of the preparation. Preferably the lipase represents about 0.7 weight percent of the preparation.

According to a preferred embodiment of the invention the surfactant employed is a lipid, which includes a fatty acid conjugated to a hydrophilic moiety. The fatty acid is preferably monolaurate, monomyristate, monopalmitate, monostearate, dilaurate, dimyristate, dipalmitate, distearate, trilaurate, trimyristate, tripalmitate or tristearate. The hydrophilic moiety is preferably a sugar, such as, but not limited to, sorbitol, sucrose, glucose and lactose, a phosphate group, a carboxylic group or a polyhydroxylated organic residue. Typically, the fatty acid and the hydrophilic moiety are conjugated via an ester bond.

According to another preferred embodiment of the invention the lipase is derived from a microorganism or a multicellular organism. Species known to be used for lipase extraction include Burkholderia sp., *Candida antarctica B*, *Candida rugosa*, Pseudomonas sp., *Candida antractica A*, *Porcine pancreas*, Humicola sp., *Mucor miehei, Rhizopus javan., Pseudomonas fluor, Candida cylindrcae, Aspergillus niger, Rhizopus oryzae, Mucor jaanicus*, Rhizopus sp., *Rhizopus japonicus* and *Candida antractica*.

According to a preferred embodiment of the invention the lipase preparation maintains lipase catalytic activity in an organic solvent. Lipase catalytic activity include hydrolysis, esterification, inter-esterification, trans-esterification, acidolysis and alcoholysis, preferably with 1,3-positional specificity with respect to triacylglycerols. The organic solvent is typically a hydrophobic solvent, such as, but not limited to, n-hexane, toluene, iso-octane, n-octane, benzene, cyclohexane and di-iso-propylether.

Further according to the present invention there is provided a method of preparing an insoluble matrix-immobilized surfactant-coated lipase complex The method includes the following method steps, wherein in a first step a lipase, an insoluble matrix and a surfactant are contacted in an aqueous solution, preferably a buffered solution. Second, conditions (e.g., sonication) are provided for the formation of the matrix-immobilized surfactant-coated lipase complex. Two alternative schemes are available in this respect. In the first the lipase is first interacted with the surfactant and only thereafter the surfactant-coated lipase is interacted with the matrix. Whereas in the second, the lipase is first interacted with the matrix and only thereafter the matrix immobilized lipase is interacted with the surfactant.

According to a preferred embodiment, the method further includes the step of separating the matrix-immobilized surfactant-coated lipase complex from the aqueous solution.

According to still another preferred embodiment of the invention the method further includes the step of drying the matrix-immobilized surfactant-coated lipase complex. Drying is preferably effected via freeze drying, fluidization or in an oven. Following drying, the matrix-immobilized surfactant-coated lipase complex preferably includes less than 100, more preferably less than 50, most preferably less than 20 parts per million water content by weight.

In a preferred embodiment of the method according to the present invention, contacting the lipase, insoluble matrix and the surfactant within the aqueous solution is effected by dissolving the surfactant in an organic solvent (e.g., ethanol) for obtaining a dissolved surfactant solution, mixing the lipase and the dissolved surfactant solution (e.g., dropwise) in the aqueous solution; sonicating the resulting suspension; and adding the insoluble matrix into the aqueous solution. Alternatively, the lipase is first interacted with the insoluble matrix and only thereafter with the surfactant.

According to a preferred embodiment, the insoluble matrix of the above-described lipase preparation is modified with a fatty acid derivative. This is to permit the immobilization of a hydrophobized lipase on a hydrophobized carrier, such as aluminium stearate, fatty-acid derivative-treated Celite and apolar or weak-polar ion-exchange resins, in order to prepare highly active enzymes.

Further according to the present invention there is provided a process of preparing structured triacylglycerols by esterification, trans-esterification, inter-esterification, acidolysis or alcoholysis between two substrates effected by contacting an insoluble matrix-immobilized surfactant-coated lipase complex with the substrates. Contacting the matrix-immobilized surfactant-coated lipase complex with the substrates is preferably effected in the presence of an organic solvent.

In a preferred embodiment, at least one of the substrates is an oil, a fatty acid or a triacylglycerol. The oil may be any of the above listed oils. The fatty acid is a medium or a short-chain fatty acid or an ester derivative thereof. A suitable fatty acid is, for example, oleic acid, palmitic acid, linolic acid, linolenic acid, stearic acid, arachidonic acid, eicosapentaenoic acid, docosahexaenoic acid and their ester derivatives.

In a preferred embodiment of the invention contacting the matrix-immobilized surfactant-coated lipase complex with the substrates is effected within a reaction reactor, e.g., a tank reactor or a fixed-bed reactor.

Further according to the present invention there is provided a process of changing the physical properties of oils/fats (e.g., triacylglycerols) by trans-esterification or inter-esterification between at least two oil/fat substrates by contacting an insoluble matrix-immobilized surfactant-coated lipase complex with the substrates, preferably in the presence of an organic solvent.

Further according to the present invention there is provided a process of changing the physical properties of long-chain triglycerides (LCT) and long-chain fatty alcohols (LCFAL) to produce wax esters by alcoholysis between at least two such substrates by contacting an insoluble matrix-immobilized surfactant-coated lipase complex with the substrates, preferably in the presence of an organic solvent.

According to a preferred embodiment, the matrix-immobilized surfactant-coated lipase complex represents 2–30 weight percent of the substrates. In another preferred embodiment the oil/fat substrates are liquid oils and solid fats. The oil may be any of the above listed oils in a native or hydrogenated form.

Further according to the present invention there is provided a triacylglycerol prepared according to the above process. The triacylglycerol serves an application such as a cocoa butter substitute, human milk fat-like, triglycerides for special diets or structured triglycerides for medical applications.

Yet further according to the present invention there is provided a preparation which includes a lipase and an organic solvent. The lipase possessing both esterification (inter- and trans-esterification), acidolysis, alcoholysis and hydrolysis catalytic activities with respect to substrates, yielding esterification and hydrolysis products, respectively. The hydrolysis products represent less than about 7, preferably less than about 5, more preferably less than about 3 weight percent of the products.

EXAMPLES

Reference is now made to the following examples, which together with the above descriptions, illustrate the invention in a non-limiting fashion.

Experimental Procedures

Materials

Different crude lipase preparations were tested in this study. Table 1 below lists commercially available lipase preparations that were employed in this study, as well as their species source and supplier. All fatty acids and triglycerides employed in this study were obtained from Fluka (Switzerland) and, as reported by the supplier, were at least 99% pure. Olive oil, sunflower oil, palm oil canola oil, corn oil and *Nigella sativa* oil were obtained from local suppliers in the Galilee area, Israel. Fish oil tris(hydroxymethyl) aminomethane and the inorganic matrices used as supports for the surfactant-coated lipase complexes, including DE, alumina and silica gel were obtained from Sigma (USA). Analytical grade n-hexane and other solvents employed, all of analytical grade, were from Bio Lab (Israel). Sorbitan fatty acid esters including sorbitan monolaurate, sorbitan monomyristate, sorbitan monopalmitate and sorbitan monostearate and sucrose fatty acid esters including mixtures of mono-, di- and tristearate sucrose esters of variable HLB values were obtained from Kao Pure Chemicals Ind. (Tokyo, Japan). Tris(Hydroxymethyl)aminomethane (tris) was from Sigma (USA). Inorganic and organic matrices used as supports for the modified lipases include diatomaceous earth (DE), alumina and silica gel; ionic exchange resins were purchased from Sigma, USA. Eupergit C and Eupergit C 250L (macroporous, spherical, approximate diameter 150 and 200 m, respectively) were from Rhom (Germany).

TABLE I

| Commercial name | Source | Manufacturer |
| --- | --- | --- |
| Lilipase A-10FG | *Rhizopus japonicus* NR 400 | Nagase, Japan |
| Saiken 100 | *Rhizopus japonicus* | Nagase, Japan |
| Lipase EC | *Aspergillus niger* | Amano, Japan |
| Lipase AY | *Candida rugosa* | Amano Japan |
| Lipase LP | *Chromobacterium viscosum* | Asahi Chem. Ind. Japan |
| Lipase PS | *Pseudomonas cepacia* | Amano, Japan |
| Lipase F | *Rhizopus oryzae* | Amano, Japan |
| Lipase F EC | *Rhizopus oryzae* | Extract Chemie-Germany |
| Newlase F | *Rhizopus niveus* | Amano, Japan |
| Lipase G | *Penicillium camembertii* | Amano, Japan |
| Lipase A | *Aspergillus niger* | Amano, Japan |
| Lipase M | *Mucor javanicus* | |

Lipase Modification and Immobilization Through Physical Adsorption

Crude enzyme was first coated with lipid surfactant or other enzyme activators e.g. gum Arabic or polyethylene glycol. A typical enzyme modification and immobilization procedure was as follows: crude enzyme (lipase, phospholipase, protease and glycosidases; protein content approximately 150 mg/L), was dissolved in IL phosphate or tris buffer solution with an appropriate pH, and magnetically stirred at 10° C. for 30 min. A lipid surfactant or other enzyme activator (0.5 g) dissolved in ethanol (20 ml) or other solvents was added dropwise into the stirred solution. The resulting enzyme solution was sonicated for 15 min and then vigorously stirred at 10° C. for 3 hours. An insoluble organic (20 g such as polypropylene, aluminium stearate or chitin) or inorganic matrix (20 g such as Celite, alumina, silica gel or ceramic support) was added into the stirred enzyme solution. The solution was magnetically stirred for a further 5 hours at 10° C. The precipitate was collected by centrifugation at 12000 rpm (Sorval Centrifuge, model RC-5B) or by filtration, and then was treated by one of two different methods as follows:

1. The wet precipitate was lyophilized after freezing overnight at −20° C. The formed powder can be directly used for batch enzymatic reactions or granulated for obtaining particulated modified and immobilized enzyme with a particle size of 50–1000 μm. The granulation process was performed using various binding reagents such as starch, methyl or ethyl cellulose, gums, agarose or other binders. For example, the granulation with starch was conducted as follows: Starch solution (4 g starch/20 ml water) was converted to gel at 70° C. The gel was cooled down to 60° C. and then introduced to the modified and immobilized enzyme wet powder. The mixture was homogenized in a high-speed mixer followed by extruding and drying at 40–60° C. for 48 hours. The immobilized enzyme was sieved to obtain particles in the range of 50–1000 μm. This particulated enzyme was used mainly in packed columns.

2. The wet precipitate formed after modification and immobilization was directly granulated with starch or other binding reagents as described above.

Enzyme modification and immobilization through ionic adsorption. The above-described modification, immobilization and granulation procedures were also used in conjunction with ion-exchange resins. The types of resin used include: strong and week basic anion exchange resins, strong and weak acidic cationic exchange resins and weak-polar and apolar ion-exchange resins. Examples of commercially available resins used in the experiments (obtained from Sigma, USA) include: Dowex 22, Dowex 1×2–400, Dowex, 2×8–100, cellulose phosphate, Amberlite IRA-95, Amberlite IRA-200, Amberlite IRA-900, Amberlite XAD-7, Amberlite XAD-16, DiannonSA-10A, Ectoela cellulose, Sephadex and sulfoxyethylcellulose. A typical modified immobilized enzyme was prepared according to the aforementioned procedure.

Enzyme Modification and Immobilization Through Covalent Binding

Two different immobilization procedures were adopted. According to the first, the enzyme was primarily coated with a surfactant and then the lipase-surfactant complex was covalently linked to an Eupergit matrix, which contains active oxirane groups. To this end, crude lipase (1 gram protein) was dissolved in 1 liter tris or phosphate buffer pH 5.8. The enzyme solution was vigorously stirred with a magnetic stirrer at 10° C. for 30 minutes. Sorbitan mono-stearate (0.5 grams) dissolved in 30 ml ethanol were added dropwise to the stirred enzyme solution. The resulting colloidal enzyme solution was sonicated for 10 minutes and then stirred for 3 hours at 10° C. Eupergit C or Eupergit C 250L (125 grams) and 12 ml solution of 5% hydrogen peroxide were added into the enzyme solution and the resulting suspension was gently handshaken for 1 minute, and then incubated for 48 hours at 23° C. The precipitate was filtered, washed with tris or phosphate buffer pH 5.8, and was freeze-dried overnight.

Figure 2:
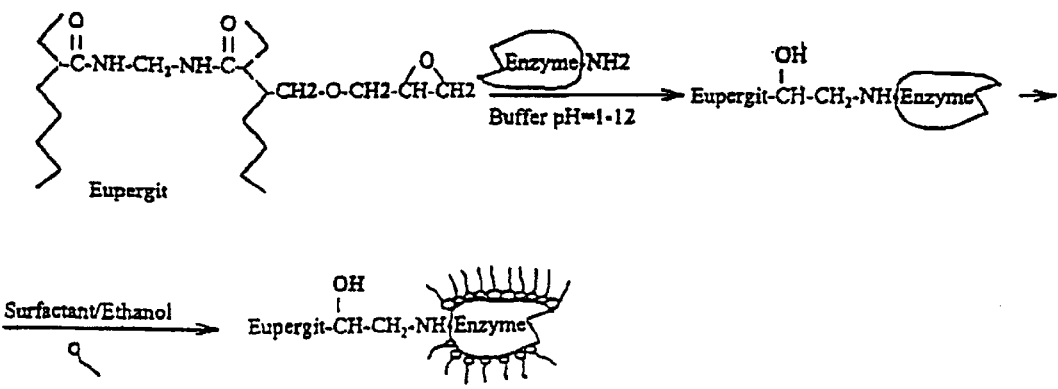
FIG. 2 depicts the chemistry associated with covalent immobilization of lipase to Eupergit C 250L followed by coating the covalently immobilized enzyme with a surfactant.

According to the second procedure, the lipase was first bound covalently to an Eupergit matrix and then the bound lipase was coated with a surfactant. The chemistry involved in this procedure is depicted in FIG. 2. To this end, crude lipase (1 gram protein) was dissolved in 1 liter tris or phosphate buffer pH 5.8. The enzyme solution was vigorously stirred with a magnetic stirrer at 10° C. for 30 minutes. Eupergit C or Eupergit C 250L (125 grams) and 12 ml solution of 5% hydrogen peroxide were added into the enzyme solution and the resulting suspension was gently handshaken for 1 minute and then incubated for 48 hours at 23° C. Sorbitan mono-stearate (0.5 grams) dissolved in 30 ml ethanol was added dropwise to the suspension under a gentle shake. The resulting suspension was sonicated for 10 minutes and incubated at 10° C. for 6 hours. The precipitate was filtered, washed with tris or phosphate buffer pH 5.8, and then freeze-dried overnight.

As a control for the activity of the covalently immobilized lipases, the same immobilization procedures were followed however without adding surfactant to the enzyme solution.

To this end, crude lipase (1 gram protein), was dissolved in 1 liter tris or phosphate buffer pH 5.8. The enzyme solution was vigorously stirred with a magnetic stirrer at 10° C. for 30 minutes. Eupergit C or Eupergit C 250L (125 grams) and 12 ml solution of 5% hydrogen peroxide were added into the enzyme solution and the resulting suspension was gently handshaken for 1 minute, and then incubated for 48 hours at 23° C. The precipitate was filtered, washed with tris or phosphate buffer pH 5.8, and then was freeze-dried overnight.

Protein determinations according to the Bradford method indicated that all enzyme preparations prepared according to this method contained 0.9–1.5 wt % protein.

Reaction Models

Three different reaction models were used to test the activity of the modified and immobilized enzymes, compared to that of the crude enzymes and of the immobilized enzymes without modification 1. Esterification reaction between lauric acid and dodecyl alcohol in an organic solvent system or in a solvent-free system.

The esterification reaction was initiated by adding 10 mg lipase preparation to 10 ml n-hexane that contained, typically, 200 mg lauric acid and 186 mg dodecyl alcohol. The reaction was magnetically stirred at 40° C. Samples were periodically withdrawn (50 μl), filtered with a Millipore filter (0.45 μm) and then mixed with a similar volume of n-hexane solution containing n-hexadecane as an internal standard, 2. Transesterification reaction between the two triglycerides; tripalmitin and tristearin in an organic solvent system or in solvent-free system.

The transesterification reaction was initiated by adding 10 mg lipase preparation to 10 ml n-hexane that contained, typically, 40 mg tripalmitin and 40 mg tristearin. The reaction was magnetically stirred at 40° C. Samples were periodically withdrawn (50 μl), filtered with a Millipore filter (0.45 μm) and then mixed with a similar volume of n-hexane solution containing n-hexadecane as an internal standard 3. Alcoholysis reaction between Olive oil and cetyl alcohol in organic solvent or solvent-free systems.

The alcoholysis reaction was initiated by adding 10 mg lipase preparation to 10 ml n-hexane that contained, typically, 500 mg olive oil, and 500 mg cetyl alcohol. The reaction solution was magnetically stirred at 40° C. Samples (50 μl) were periodically removed, filtered with Millipore filters (0.45 m) and then mixed with a similar volume of n-hexane solution containing tridecanoin as an internal standard.

Unless otherwise indicated, all experiments were conducted under the above-described conditions. Each esterification reaction was carried out in duplicate. In all experiments, n-hexane was dried over molecular sieves to minimize its water content down to 6 mg/liter. Thus, water concentration in all reaction systems was less than 30 mg/liter.

Protein Content

The protein content of the modified lipases, and the modified and immobilized lipases was determined by the microkejldahi method.

Enzyme Activity in a Batch System

The activity of the activated modified enzyme, modified and immobilized enzyme on insoluble matrix, crude enzymes and immobilized enzymes in insoluble matrix, was tested using a 1 ml vials containing the substrates. The vials were shaken at 40° C. and samples were analyzed after certain time intervals. Reaction rates were determined at substrate conversions less than 7% per mg of protein.

Operational Stability of Modified and Immobilized Enzyme

The operational stability of the particulated modified and immobilized enzymes was tested in a jacketed column reactor (0.5 cm i.d. and 15 cm long) using the alcoholysis of olive oil and cetyl alcohol in n-hexane as a reaction model. The enzyme particles were packed in the column and the substrate solution was recirculated through the packed enzyme. The circulation was stopped after one hour and the reaction solution was analyzed. After each run the solution was discarded and the packed immobilized enzyme was washed with organic solvent (n-hexane) before charging a fresh substrate solution. This procedure was repeated 10–20 times.

EXPERIMENTAL RESULTS

Example 1

Protein Content of the Lipase Preparations

The protein content of the different crude lipases, lipases modified with sorbitan monostearate (SMS), lipases immobilized on Celite and SMS-modified lipases immobilized on Celite, was measured as described above. The results are shown in Table II below.

The results show that there is fairly wide variation in protein concentration between the various preparations. For the surfactant-coated, matrix-immobilized enzymes, the protein content varied from 0.05% to 1.12%, by weight, according to the enzyme used in the preparation. Similar variation was seen when one enzyme, Lilipase, was treated with different lipid surfactants or other activating agents, and, optionally, immobilized on Celite. The results of this investigation are shown in Table III.

TABLE II

| Enzyme | Protein content (%) |
| --- | --- |
| Lilipase A-10FG | |
| Lipase crude | 4.6 |
| Lipase + SMS | 1.62 |
| Lipase + SMS/Celite | 0.11 |
| Lipase/Celite | 0.1 |
| Lipase M | |
| Lipase crude | 0.96 |
| Lipase + SMS | 1.8 |
| Lipase + SMS/Celite | 0.12 |
| Lipase/Celite | 0.1 |
| Lipase G - Amano 50 | |
| Lipase crude | 9.65 |
| Lipase + SMS | 1.11 |
| Lipase + SMS/Celite | 0.06 |
| Lipase/Celite | 0.29 |
| Lipase A - Amano 6 | |
| Lipase crude | 21.63 |
| Lipase + SMS | 4.85 |
| Lipase + SMS/Celite | 0.225 |
| Lipase/Celite | 0.2 |
| Lipase Saiken 100 | |
| Lipase crude | 4.84 |
| Lipase + SMS | 2.87 |
| Lipase + SMS/Celite | 0.06 |
| Lipase/Celite | 0.04 |
| Lipase F P-15 | |
| Lipase crude | 49.2 |
| Lipase + SMS | 9.31 |
| Lipase + SMS/Celite | 0.70 |
| Lipase/Celite | 0.47 |
| Lipase F - EC | |
| Lipase crude | 49.7 |
| Lipase + SMS | 7.2 |

TABLE II-continued

| Enzyme | Protein content (%) |
| --- | --- |
| Lipase + SMS/Celite | 1.12 |
| Lipase/Celite | 0.2 |
| Lipase EC | |
| Lipase crude | 36.8 |
| Lipase + SMS | 6.5 |
| Lipase + SMS/Celite | 0.48 |
| Lipase/Celite | 0.39 |
| Lipase PS | |
| Lipase crude | 7.5 |
| Lipase + SMS | 0.72 |
| Lipase + SMS/Celite | 0.16 |
| Lipase/Celite | 0.08 |
| Lipase Newlase F | |
| Lipase crude | 25.1 |
| Lipase + SMS | 2.17 |
| Lipase + SMS/Celite | 0.24 |
| Lipase/Celite | 0.013 |
| Lipase LP | |
| Lipase crude | 6.16 |
| Lipase + SMS | 4.6 |
| Lipase + SMS/Celite | 0.65 |
| Lipase/Celite | 0.21 |
| Lipase AY - Amano 30 | |
| Lipase crude | 5.14 |
| Lipase + SMS | 2.6 |
| Lipase + SMS/Celite | 0.05 |
| Lipase/Celite | 0.05 |

TABLE III

| Enzyme | Protein content (%) |
| --- | --- |
| Lilipase + sorbitan monostearate | 1.614 |
| Lilipase + sorbitan monostearate/Celite | 0.112 |
| Lilipase + sucrose ester HLB = 5 | 1.0 |
| Lilipase + sucrose ester HLB = 5/Celite | 0.128 |
| Lilipase + sucrose ester HLB = 11 | 0.15 |
| Lilipase + sucrose ester HLB = 11/Celite | 0.051 |
| Lilipase + sucrose ester HLB = 16 | 0.1 |
| Lilipase + sucrose ester HLB = 16/Celite | 0.04 |
| Lilipase + sorbitan monolaurate | no precipitate |
| Lilipase + sorbitan monolaurate/Celite | 0.128 |
| Lilipase + sorbitan tristearate | 1.436 |
| Lilipase + sorbitan tristearate/Celite | 0.134 |
| Lilipase + sorbitan trioleate | no precipitate |
| Lilipase + sorbitan trioleate/Celite | 0.115 |
| Lilipase + monooleate | no precipitate |
| Lilipase + monooleate/Celite | 0.140 |
| Lilipase + lecithin | no precipitate |
| Lilipase + lecithin/Celite | 0.16 |
| Lilipase + stearic acid | 1.65 |
| Lilipase + stearic acid/Celite | 0.108 |
| Lilipase + Octadecanoic acid | 1.17 |
| Lilipase + Octadecanoic acid/Celite | 0.102 |
| Lilipase polyoxyethylene-8-stearate | 2.35 |
| Lilipase polyoxyethylene-8-stearate/Celite | 0.115 |
| Lilipase + polyethyleneglycol | no precipitate |
| Lilipase + polyethyleneglycol/Celite | 0.10 |
| Lilipase gum Arabic | no precipitate |
| Lilipase gum Arabic/Celite | 0.172 |

Example 2

Esterification, Transesterification and Alcoholysis Activities of the Lipase Preparations A comparison was made of the enzymatic activities of the various lipase preparations (prepared as described above).

For the purposes of this comparison, the results (shown in Table IV) are presented as reaction rates (ri).

TABLE IV

| Enzyme | ri (esterification) ($\mu$mol/min · mg protein) | ri (transesterification) ($\mu$mol/min · mg protein) | ri (alcoholysis) ($\mu$mol/min · mg protein) |
|---|---|---|---|
| *Lilipase A-10FG* | | | |
| Crude | 0.16 | 0.01 | 0 |
| Lipase + SMS | 7.43 | 5.2 | 2.1 |
| Lipase + SMS/Celite | 27.4 | 18.1 | 7.1 |
| Lipase/Celite | 4.5 | 0.8 | 0.4 |
| *Lipase M* | | | |
| Crude | 0.2 | 0 | 0 |
| Lipase + SMS | 6.7 | 4.8 | 2.0 |
| Lipase + SMS/Celite | 22.3 | 16.4 | 6.7 |
| Lipase/Celite | 3.2 | 0.1 | 0.3 |
| *Lipase PS* | | | |
| Crude | 0.3 | 0 | 0 |
| Lipase + SMS | 5.2 | 4.3 | 1.6 |
| Lipase + SMS/Celite | 18.3 | 12.5 | 6.5 |
| Lipase/Celite | 4.5 | 0.4 | 0.2 |
| *Lipase LP* | | | |
| Crude | 0.3 | 0 | 0 |
| Lipase + SMS | 4.9 | 3.3 | 1.4 |
| Lipase + SMS/Celite | 15.5 | 9.5 | 2.8 |
| Lipase/Celite | 2.3 | 0.2 | 0.35 |
| *Lipase EC* | | | |
| Crude | 0 | 0 | 0 |
| Lipase + SMS | 0.7 | 1.9 | 1.9 |
| Lipase + SMS/Celite | 1.9 | 10.3 | 5.4 |
| Lipase/Celite | 0.1 | 1.1 | 0.3 |
| *Lipase AY Amano 30* | | | |
| Crude | 0 | 0 | 0 |
| Lipase + SMS | 2.2 | 0.3 | 0.7 |
| Lipase + SMS/Celite | 16.3 | 0.8 | 1.3 |
| Lipase/Celite | 0.9 | 0.05 | 0.4 |
| *Lipase G* | | | |
| Crude | 0 | 0 | 0 |
| Lipase + SMS | 0.1 | 0.15 | 0 |
| Lipase + SMS/Celite | 1.4 | 0.4 | 0 |
| Lipase/Celite | 0.1 | 0 | 0 |
| *Lipase A* | | | |
| Crude | 0 | 0 | 0 |
| Lipase + SMS | 0.9 | 0.5 | 0.1 |
| Lipase + SMS/Celite | 3.0 | 1.2 | 0.6 |
| Lipase/Celite | 0.3 | 0.1 | 0 |
| *Lipase F-AP15* | | | |
| Crude | 0.3 | 0 | 0 |
| Lipase + SMS | 6.7 | 4.9 | 1.9 |
| Lipase + SMS/Celite | 26.4 | 12.7 | 5.4 |
| Lipase/Celite | 0.8 | 0.93 | .3 |
| *Lipase F-EC* | | | |
| Crude | 0.4 | 0 | 0 |
| Lipase + SMS | 7.1 | 3.4 | 1.5 |
| Lipase + SMS/Celite | 23.5 | 10.5 | 5.4 |
| Lipase/Celite | 1.9 | 0.6 | 0.6 |
| *Lipase Saiken 100* | | | |
| Crude | 0.15 | 0 | 0 |
| Lipase + SMS | 6.9 | 4.2 | 2.4 |
| Lipase + SMS/Celite | 29.3 | 10.3 | 8.2 |
| Lipase/Celite | 1.2 | 3.2 | 0.4 |
| *Lipase Newlase F* | | | |
| Crude | 0 | 0 | 0 |
| Lipase + SMS | 1.3 | 1.3 | 0.4 |
| Lipase + SMS/Celite | 6.4 | 6.8 | 0.5 |
| Lipase/Celite | 0.2 | 0.1 | 0 |

These results indicate that in their native form the crude lipases used in this study lack measurable esterification or transesterification activity with the low water concentrations used. In contrast, both modification with the surfactant sorbitan monostearate and, independently, immobilization onto Celite, resulted in detectable levels of esterification and transesterification. When the enzyme was subjected to both of these treatments, however, the reaction rates of both the esterification and transesterification reactions studies increased to much greater levels. From the numerical results presented in Table IV, it is clear that there is an unexpected synergism between the two stages of modification, i.e., treatment with surfactant and immobilization onto the matrix.

Figure 3:
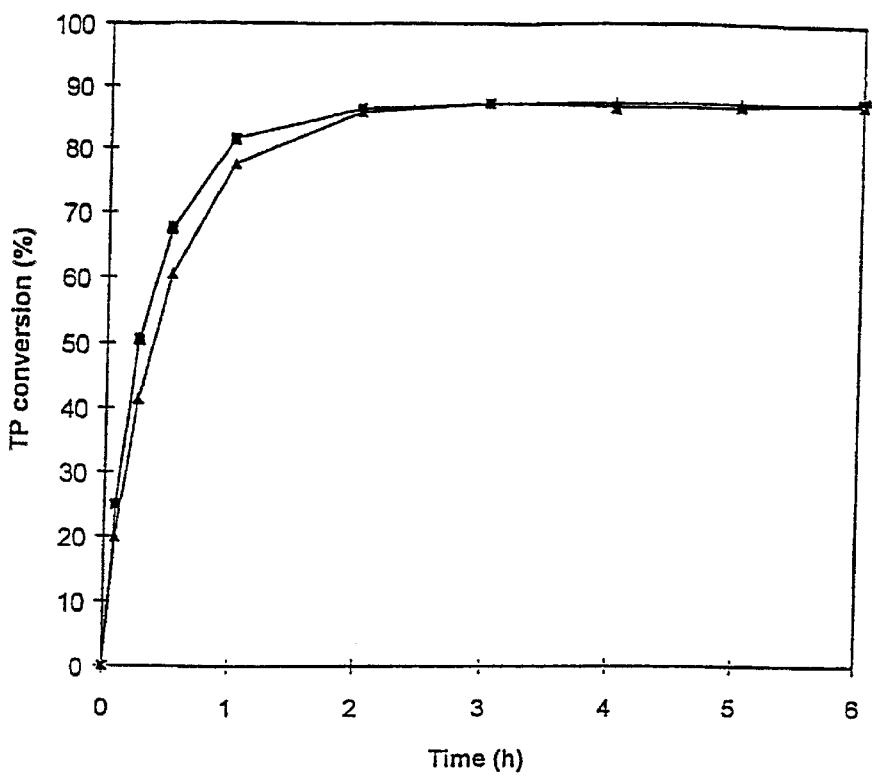
FIG. 3 presents inter-esterification reaction profiles of physically immobilized lipases. Reaction conditions were 50 mg tripalmitin, 35 mg capric acid and 20 mg surfactant-coated lipase (Saiken 100—triangles, or Lilipase A10-FG -squares) immobilized on DE in 10 ml n-hexane. The reaction system was magnetically stirred and thermostated at 40° C.
Figure 4:
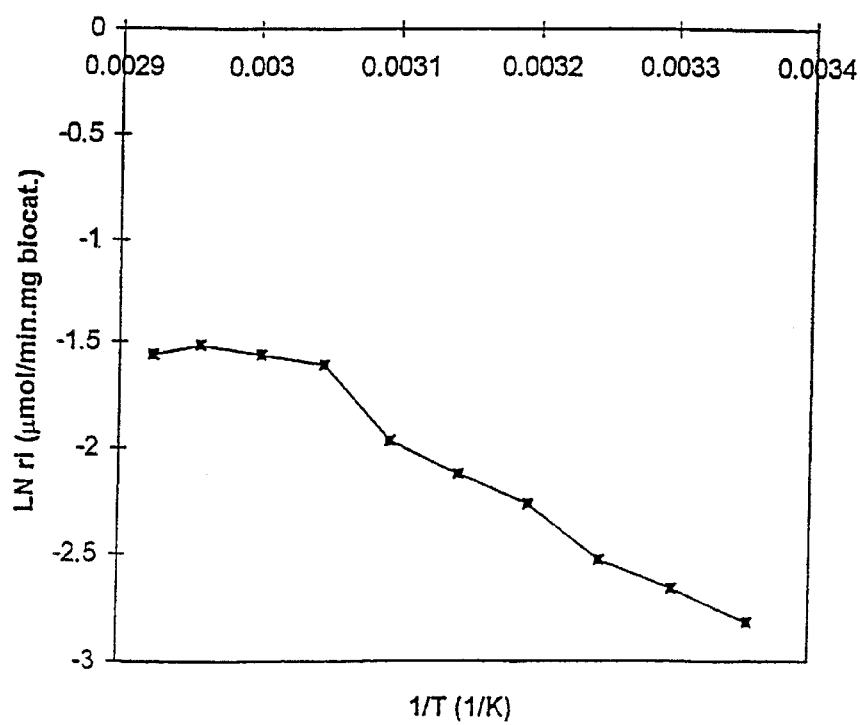
FIG. 4 presents an Arrhenius plot for the inter-esterification reaction of tripalmitin and capric acid with DE-physically immobilized surfactant-coated Lilipase A10-FG.

FIG. 3 presents the conversion of tripalmitin with time when DE-immobilized surfactant-coated Saiken-100 (triangles) and Lilipase 10-FG (squares) were used to catalyze the inter-esterification reaction of tripalmitin and capric acid. The inter-esterification reaction rates thus measured were 0.096 and 0.104 mmol/min.mg biocatalyst, respectively.

Example 3

Fatty acid specificity of immobilized surfactant-coated lipase complexes The specificity of the inorganic matrix-immobilized surfactant-coated lipase complexes of the present invention toward different fatty acid substrates was tested by monitoring the inter-esterification of fatty acids of various chain lengths with tripalmitin. The results are summarized in Table V below. Reaction-conditions were as follows: Inter-esterification activity of crude lipase preparations was tested in n-hexane using tripalmitin (50 mg) as a triacylglycerol substance and capric acid (35 mg) as a medium-chain fatty acid substance. Inter-esterification activities of 10 mg non-immobilized surfactant-coated lipase (5–10% protein content), or of 20 mg of inorganic matrix surfactant-coated lipase (0.2–2% protein content), in n-hexane (10 ml), were examined using the same substrates.

TABLE V

| Fatty acid | Fatty acid chain length | Inter-esterification rate (mmol/min · mg biocat. |
|---|---|---|
| Butyric acid | (C4) | 0.055 |
| Hexanoic acid | (C6) | 0.06 |
| Octanoic acid | (C8) | 0.09 |
| Decanoic acid | (C10) | 0.104 |
| Lauric acid | (C12) | 0.15 |
| Myristic acid | (C14) | 0.2 |
| Palmitic acid | (C16) | 0.25 |
| Stearic acid | (C18) | 0.26 |
| Oleic acid | (C18:1) | 0.3 |
| Arachidonic acid | (C20) | 0.28 |
| Behenic acid | (C22) | 0.28 |

From Table V it can be seen that the immobilized surfactant-coated Lilipase complexes according to the present invention predominantly catalyzed the inter-esterification of fatty acids and tripalmitin with 1,3-positional specificity. The concentration of hydrolysis products did not exceed 5 wt % of the initial tripalmitin concentration.

It is further noted that the inter-esterification activity of the inorganic matrix-immobilized surfactant-coated lipase complexes according to the present invention was affected by the fatty acid chosen to be used as a substrate. Thus, fatty acids having longer alkyl chains, such as palmitic and stearic acids, are better substrates for the DE-immobilized surfactant-coated lipase complexes than fatty acids having shorter alkyl chains.

Example 4

Influence of Surfactant Choice on Inorganic Matrix-immobilized Surfactant-coated Lipase Complexes Table VI below demonstrates that the type of sorbitan fatty acid ester selected for coating the lipase influences the inter-esterification activity of Celite-immobilized surfactant-coated lipase complexes.

When sorbitan monostearate was used for coating, the inter-esterification activity of the complex was the highest. However, using a shorter fatty acid chain length in the sorbitan ester led to decrease in the activity of the complex.

TABLE VI

| Enzyme | ri (esterification) (mol/min · mg protein) | ri (transesterication) (mol/min · mg protein) | ri (alcoholysis) ((mol/min · mg protein) |
|---|---|---|---|
| Lilipase A-10FG | | | |
| Lilipase crude | 0.16 | 0.01 | 0 |
| Lilipase/Celite | 4.5 | 0.1 | 0.4 |
| Lilipase + sorbitan monostearate | 7.43 | 5.75 | 1.2 |
| Lilipase + sorbitan monostearate/Celite | 27.4 | 15.5 | 2.3 |
| Lilipase + sucrose ester HLB = 5 | 23.6 | 4.5 | 3.5 |
| Lilipase + sucrose ester HLB = 5/Celite | 22.4 | 7.5 | 5.5 |
| Lilipase + sucrose ester HLB = 11 | 31.1 | 12.5 | 6.2 |
| Lilipase + sucrose ester HLB = 11/Celite | 25.3 | 30 | 8.2 |
| Lilipase + sucrose ester HLB = 16 | 8.5 | 2 | 1.1 |
| Lilipase + sucrose ester HLB = 16/Celite | 16.2 | 12.5 | 4.2 |
| Lilipase + sorbitan monolaurate | 6.2 | 4 | 0.6 |
| Lilipase + Sorbitan monolaurate/Celite | 7.1 | 11.5 | 2.1 |
| Lilipase + sorbitan tristearate | 10.1 | 4 | 1.9 |
| Lilipase + sorbitan tristearate/Celite | 22.5 | 31 | 7.2 |
| Lilipase + sorbitan trioleate | 18.3 | 7.5 | 2.6 |
| Lilipase + sorbitan trioleate/Celite | 27.3 | 20 | 9.3 |
| Lilipase + sorbitan monooleate | 6.2 | 2.5 | 1.4 |
| Lilipase + monooleate/Celite | 8.5 | 10 | 4.2 |
| Lilipase + lecithin | 10.2 | 3.5 | 1.15 |
| Lilipase + lecithin/Celite | 16.2 | 10 | 3.2 |
| Lilipase + stearic acid | 6.3 | 3.75 | 1.6 |
| Lilipase + stearic acid/Celite | 13.4 | 14 | 5.3 |
| Lilipase + Octadecanoic acid | 6.2 | 3 | 0.81 |
| Lilipase + Octadecanoic acid/Celite | 14.6 | 11.5 | 3.4 |
| Lilipase polyoxyethylene-8-stearate | 6.5 | 4.4 | 2.1 |
| Lilipase polyoxyethylene-8-stearate/Celite | 13.5 | 16 | 6.2 |
| Lilipase + polyethylenglycol | 5.4 | 0 | 0 |
| Lilipase + polyethylenglycol/Celite | 9.2 | 0.4 | 0.4 |
| Lilipase gum Arabic | 9.3 | 2 | 0.5 |
| Lilipase gum Arabic/Celite | 11.1 | 5 | 1.1 |

Example 5

Physical Binding of Modified Lipase to Insoluble Matrices

The esterification, transesterification and alcoholysis activity for Lilipase A-10FG immobilized on various insoluble matrices was measured, and compared with the activities of Lilipase A-10FG modified with sorbitan monostearate and immobilized on different inorganic matrices. The results are shown in Table VII.

TABLE VII

| Enzyme/Insoluble matrix* | ri (esterification) ($\mu$mol/min · mg protein) | ri (transesterification) ($\mu$mo/min · mg protein) | ri (alcoholysis) ($\mu$mol/min · mg protein) |
|---|---|---|---|
| Lilipase A10-FG crude | 0.16 | 0.01 | 0 |
| Lilipase + SMS | 7.43 | 5.2 | 2.1 |
| Lilipase + SMS/Celite (acid-washed) | 27.4 | 18.1 | 7.1 |
| Lilipase/Celite (acid-washed) | 4.5 | 0.8 | 0.4 |
| Lilipase + SMS/Celite acid-nonwashed) | 25.4 | 13.5 | 6.0 |
| Lilipase/Celite acid-nonwashed | 3.5 | 0.5 | 0.1 |
| Lilipase + SMS/fatty* acid-treated Celite | 41.3 | 27.4 | 17.3 |
| Lilipase/fatty acid-treated Celite | 19.7 | 9.5 | 4.6 |
| Lilipase + SMS/Alumina | 23.2 | 11.1 | 5.4 |
| Lilipase/Alumina | 1.6 | 0.3 | 0.4 |
| Lilipase + SMS/Aluminium monostearate | 45.3 | 29.1 | 19.2 |
| Lilipase/Aluminium monostearate | 19.2 | 9.8 | 6.1 |
| Lilipase + SMS/Silica | 21.3 | 10.8 | 5.7 |
| Lilipase/Silica | 3.2 | 0.4 | 0.2 |
| Lilipase + SMS/Calcium carbonate | 18.6 | 12.3 | 6.1 |
| Lilipase/Calcium carbonate | 2.4 | 0.4 | 0.2 |
| Lilipase + SMS/Calcium sulfate | 16.6 | 11.3 | 5.6 |
| Lilipase/Calcium sulfate | 0.3 | 0.2 | 0.3 |

*Fatty acid-(or its derivative) treated Celite (hydrophobized Celite) was prepared as follows: Celite (100 g) was suspended in phosphate buffer solution (100 ml) of pH = 5.7. A solution of free fatty acid or its derivative (stearic acid or fatty acid sugar ester) dissolved in ethanol (5 g/30 ml) was added dropwise to the vigorously stirred suspension at 70° C. The suspension was stirred for 2 h, filtered, washed with water and then lyophilized.

The most suitable carriers for the immobilized enzymes used in this study are aluminum monostearate and fatty acid-treated Celite. As can be seen in Table VII, nonmodified Lilipase immobilized on Aluminum monostearate or fatty acid treated-Celite gave relatively good activity in all of the three reaction models. The results presented in this Table prove that the enzyme modification with a surfactant in a first step and then immobilizing the modified enzyme on a fatty acid-treated insoluble matrix leads to a further increment in the activity of the enzyme. As can be seen in the above Table, the activity of the fatty acid derivative-modified and immobilized lipase on a fatty acid derivative-treated insoluble matrix (Aluminum monostearate, fatty acid derivative-treated Celite) is much greater than the activity of lipase immobilized on a fatty acid derivative-treated insoluble matrix

Example 6

The Effect of the Choice of Ion-exchange Resin on Enzyme Activity

The esterification, transesterification and alcoholysis activities of Lilipase A-10FG immobilized on various ion-exchange resins, and of the same enzyme modified with sorbitan monostearate prior to immobilization were compared. The results of this comparison (expressed as reaction rate, ri) are shown in Table VIII.

TABLE VIII

| Lilipase/<br>Ion-exchange<br>resin* | ri (esterification)<br>($\mu$mol/<br>min · mg<br>protein) | ri (trans-esterification)<br>($\mu$mol/<br>min · mg<br>protein) | ri (alcoholysis)<br>($\mu$mol/<br>min · mg<br>protein) |
|---|---|---|---|
| Dowex 22 | 4.9 | 4.7 | 1.9 |
| Dowex 22 + SMS | 32.2 | 23.1 | 6.3 |
| Dowex 1x2-400 | 6.9 | 3.5 | 1.1 |
| Dowex 1x2-400 + SMS | 29.6 | 25.4 | 6.1 |
| Dowex2x8-100 | 5.5 | 4.7 | 2.2 |
| Dowex2x8-100 + SMS | 21.3 | 16.2 | 7.3 |
| Cellulose phosphate | 3.5 | 0.2 | 0.1 |
| Cellulose phosphate + SMS | 6.3 | 1.5 | 1.1 |
| Amberlite IRA-95 | 7.6 | 0.8 | 0.9 |
| Amberlite IRA-95 + SMS | 26.2 | 12.5 | 2.3 |
| Amberlite IRA-200 | 9.2 | 3.1 | 1.4 |
| Amberlite IRA-200 + SMS | 28.6 | 18.9 | 5.3 |
| Amberlite IRA-900 | 6.1 | 4.2 | 2.3 |
| Amberlite IRA-900 + SMS | 37 | 28.3 | 8.6 |
| DiannonSA-10A | 6.1 | 2.8 | 1.2 |
| DiannonSA-10A + SMS | 31 | 19.5 | 11.3 |
| Ectoela cellulose | 5.4 | 2.3 | 1.7 |
| Ectoela cellulose + SMS | 29.5 | 12.2 | 5.7 |
| Sephadex | 1.5 | 0.2 | 0.1 |
| Sephadex + SMS | 2.9 | 0.9 | 0.8 |
| Sulfoxyethylcellulose | 5.6 | 3.2 | 2.5 |
| Sulfoxyethylcellulose + SMS | 32.3 | 17.0 | 12.6 |
| Amberlite XAD-7 (Weak-polar) | 8.3 | 4.5 | 3.8 |
| Amberlite XAD-7 + SMS | 37.3 | 29.5 | 17.5 |
| Amberlite XAD-16 (apolar) | 6.7 | 6.5 | 4.3 |
| Amberlite XAD-16 + SMS | 33.4 | 24.4 | 14.3 |

*All ion-exchange resins were purchased from Sigma, USA.

These results demonstrate the dramatic increase in esterification and trans-esterification activity of the modified enzymes upon immobilization. Furthermore, it can be seen from Table VIII that ion-exchange resins containing hydrophobic groups in their structure behave much better as carriers for the surfactant-modified enzymes.

Example 7

Biosynthesis of Structured Triglycerides from Different Oils Using Inorganic Matrix-immobilized Surfactant-coated Lipase Complexes Table IX below demonstrates the rates of inter-esterification reactions between different oils and capric acid in n-hexane system and in a solvent free system at 60° C. The interesterification reactions were catalyzed by DE-immobilized surfactant-Lilipase A10-FG complexes.

DE-immobilized surfactant-Lilipase complexes predominantly catalyzed the inter-esterification of various oils with capric acid in n-hexane and solvent free systems. The highest inter-esterification reaction was obtained when olive oil was employed. Similar reaction rates where obtained when the inter-esterification reactions were carried-out in a solvent-free system.

TABLE IX

| Source of oil | R.R. (mmol/min · mg biocat.) in n-hexane | R.R. (mmol/min · mg biocat.) in solvent free system |
|---|---|---|
| Olive oil | 0.52 | 0.73 |
| Fish oil | 0.4 | 0.53 |
| Sun flower oil | 0.3 | 0.42 |
| Palm oil | 0.2 | 0.31 |
| Canola oil | 0.32 | 0.45 |
| Corn oil | 0.24 | 0.41 |
| *Nigella sativa* oil | 0.2 | 0.46 |

Example 8

Operational Stability of Modified and Immobilized Enzymes

The stability of the enzyme preparations over repeated cycles of use was determined as described in the methods section above. For the purposes of this investigation, Lilipase A-10FG was used to catalyze the conversion of olive oil to a wax ester. Activity was measured in a 10-run experiment, each run requiring one hour for completion. The level of activity was measured as percentage conversion of the olive oil. The reaction conditions used were as follows:

100 ml of n-Hexane containing 20 g olive oil and 20 g cetyl alcohol recirculated over an immobilized enzyme packed-bed at a circulation rate of 2.3 ml/min at 40° C. The column used to pack the granulated enzyme was 12 cm long with an internal diameter of 0.75 cm. The results of this investigation are shown in FIGS. 5–12.

Figure 5:
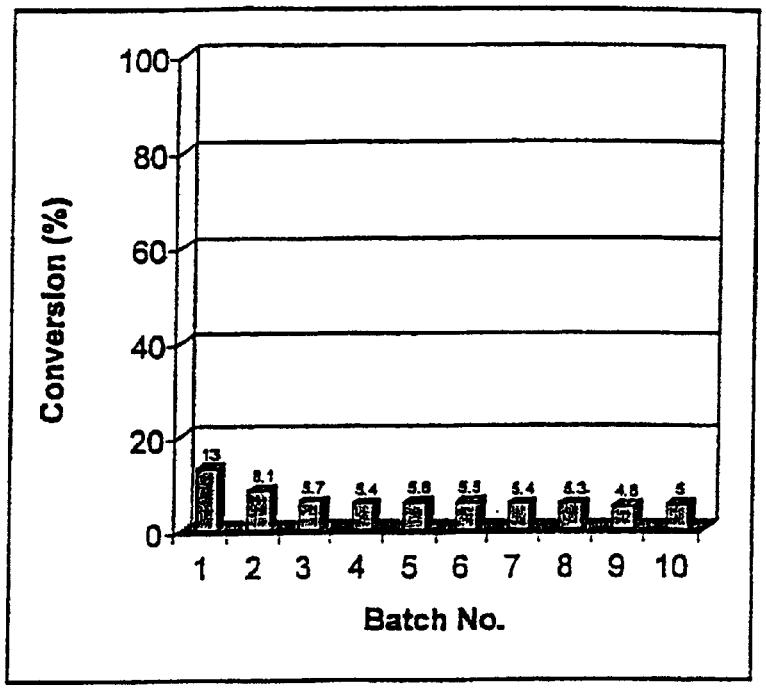
FIG. 5 is a bar graph showing the functional stability of Lilipase A 10FG immobilized on Celite and granulated with 2% starch.
Figure 6:
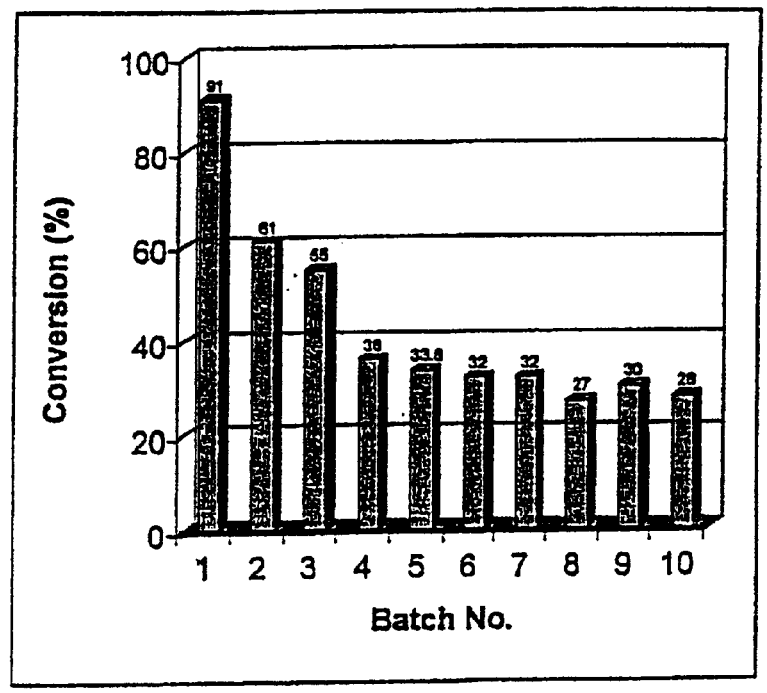
FIG. 6 is a bar graph showing the functional stability of powdered Lilipase A 10FG modified with sorbitan monostearate and immobilized on Celite.
Figure 7:
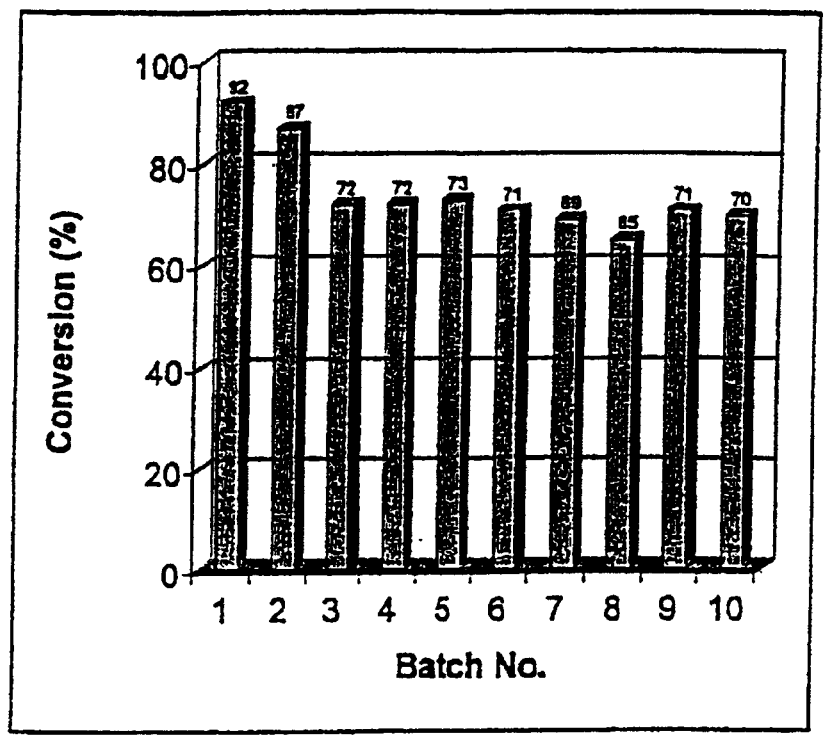
FIG. 7 is a bar graph showing the functional stability of Lilipase A 10FG modified with sorbitan monostearate, immobilized on Celite and granulated with 2% starch.

FIG. 5 shows that the activity of Lilipase A-10FG immobilized on Celite (without modification) and granulated with 2% starch was low, and that the activity decreased with each re-use. FIG. 6 shows that the activity of the same lipase powder after modification with sorbitan monostearate and then immobilization on Celite (without granulation) was 9-fold higher than the activity of the same non-modified lipase. It can be seen from FIG. 2 that there was sharp activity loss after the first, second and the third runs, which can be attributed to washing out of the immobilized enzyme. FIGS. 7–16 show that the enzyme activity in organic solvent can be essentially retained by granulation with different binding reagents such as starch, ethyl cellulose, gums, starch, etc. The granulation process also facilitates the flow in the packed column with enzyme. The binders used in these figures are as follows:

FIG. 7 Starch 2%

Figure 8:
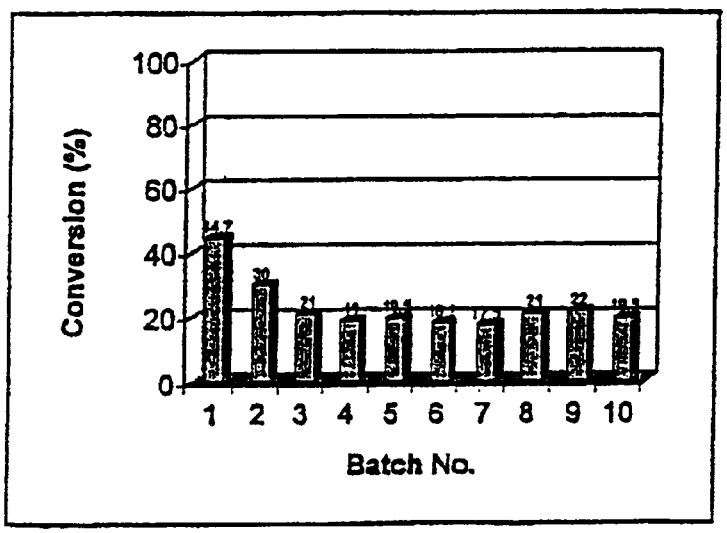
FIG. 8 is a bar graph showing the functional stability of Lilipase A 10FG modified with sorbitan monostearate, immobilized on Celite and granulated with ethyl cellulose.

FIG. 8 Ethyl cellulose 2%

Figure 9:
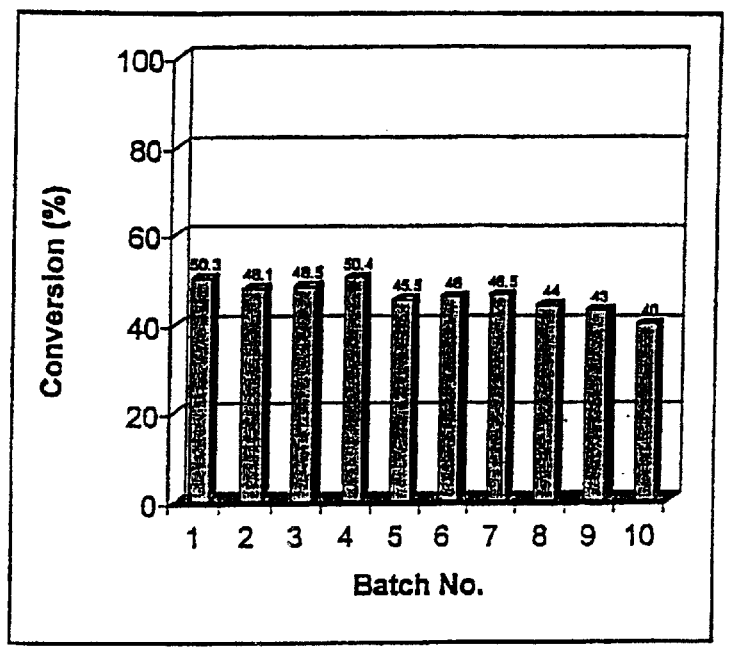
FIG. 9 is a bar graph showing the functional stability of Lilipase A 10FG modified with sorbitan monostearate, immobilized on Celite and granulated with 2% gum Arabic.

FIG. 9 Gum Arabic 2%

Figure 10:
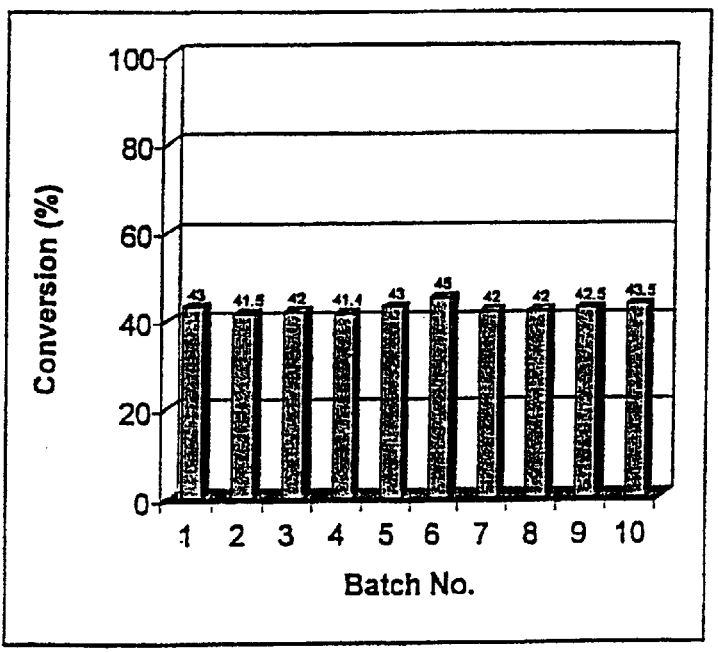
FIG. 10 is a bar graph showing the functional stability of Lilipase A 10FG modified with sorbitan monostearate, immobilized on Amberlite IRA-900 and granulated with ethyl cellulose.

FIG. 10 Ethyl cellulose 2%

FIG. 11 Agarose 2%

FIG. 12 Starch 4%

FIGS. 13–16 Starch 2%

Figure 11:
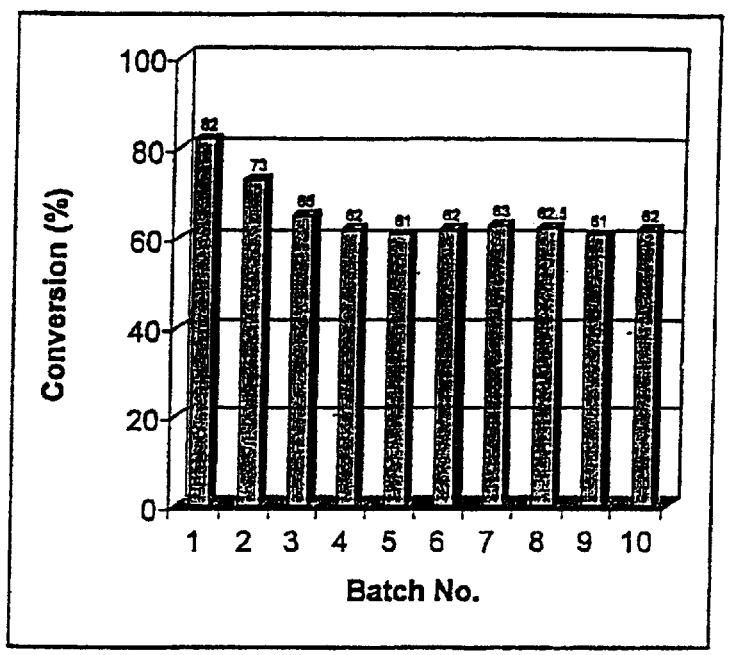
FIG. 11 is a bar graph showing the functional stability of Lilipase A 10FG modified with sorbitan monostearate, immobilized on Celite and granulated with 2% agarose.
Figure 12:
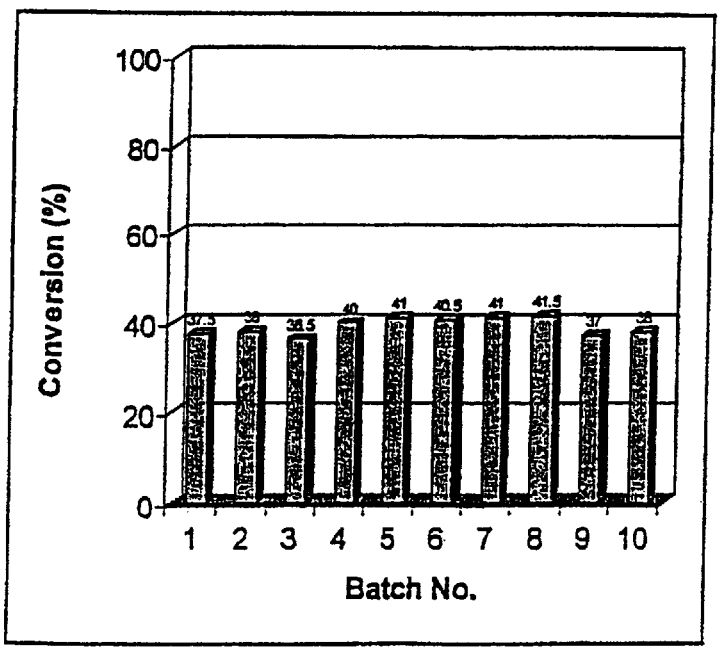
FIG. 12 is a bar graph showing the functional stability of Lilipase A 10FG modified with sorbitan monostearate, immobilized on Celite and granulated with 4% starch.
Figure 13:
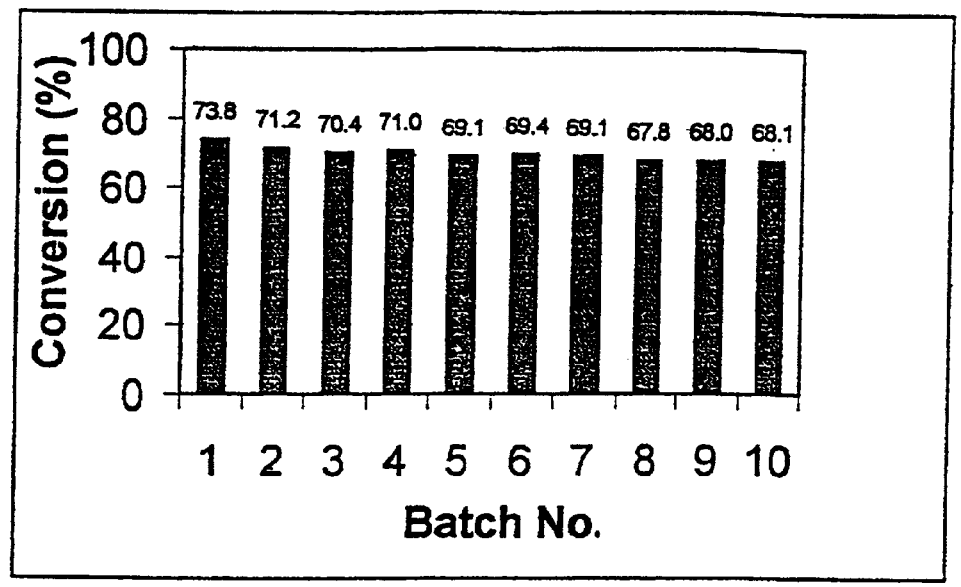
FIG. 13 is a bar graph showing the functional stability of Lilipase A 10FG modified with sorbitan tristearate, immobilized on Celite and granulated with 2% starch.
Figure 14:
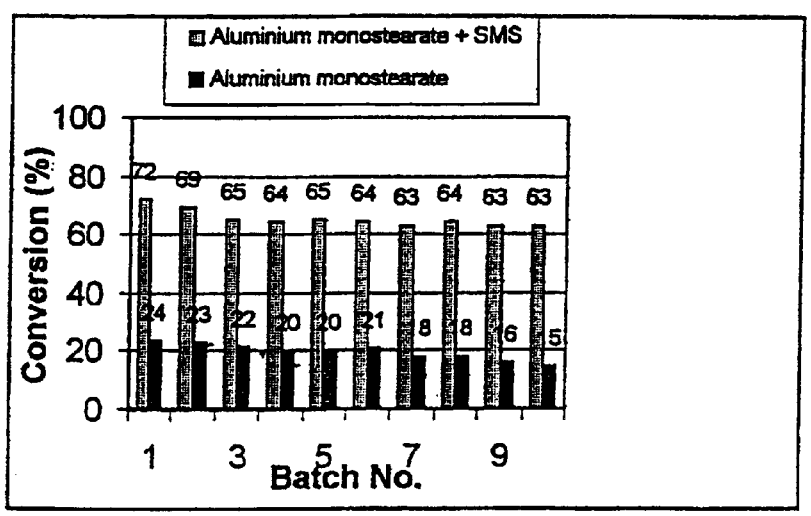
FIG. 14 is a bar graph showing the functional stability of Lilipase A 10FG modified with sorbitan monostearate, immobilized on aluminium monostearate and granulated with 2% starch. The graph also shows comparable results for unmodified enzyme, immobilized on aluminium monostearate and granulated with 2% starch.
Figure 15:
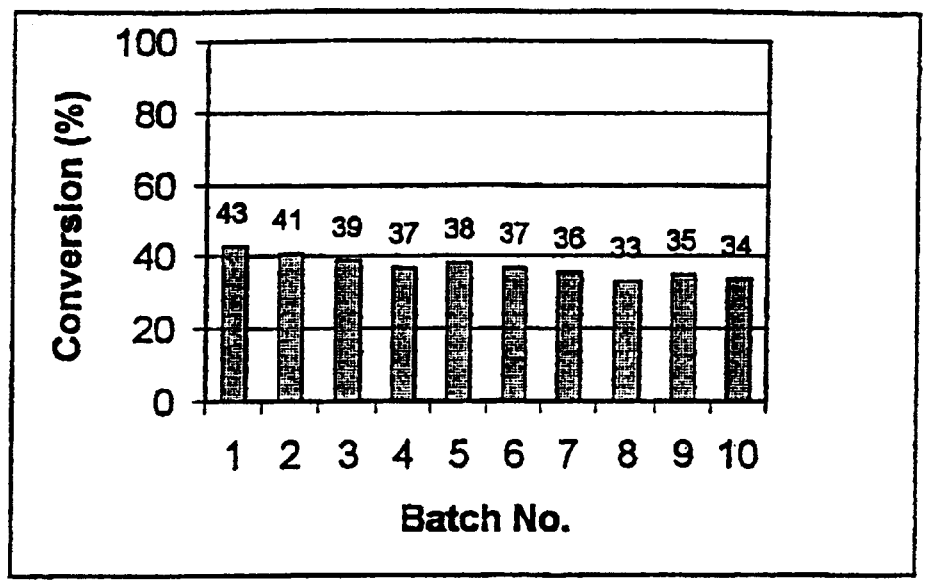
FIG. 15 is a bar graph showing the functional stability of Lilipase A 10FG modified with sorbitan monostearate, immobilized on Amberlite XAD-16 and granulated with 2% starch.
Figure 16:
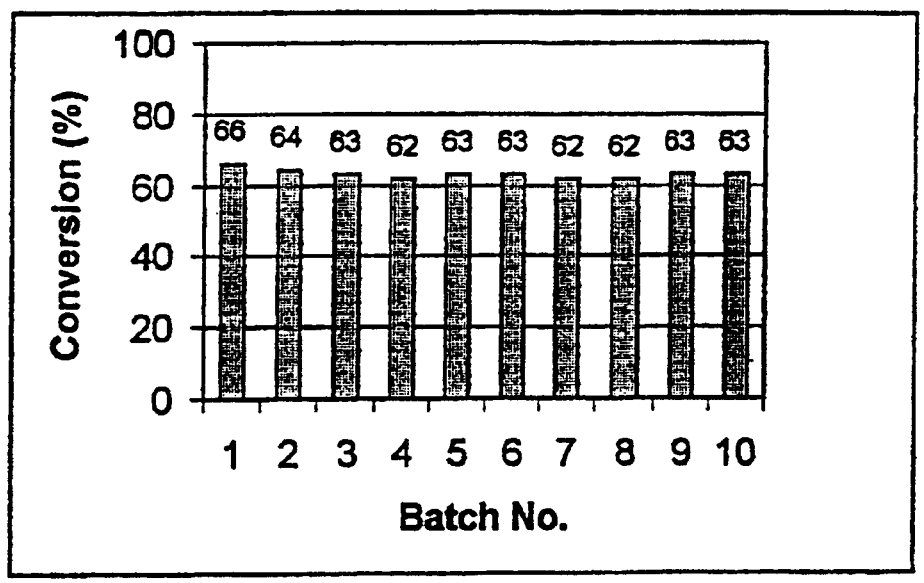
FIG. 16 is a bar graph showing the functional stability of Lilipase A 10FG modified with sorbitan monostearate, immobilized on Amberlite XAD-7 and granulated with 2% starch.

Immobilization was performed on Celite in the experiments shown in FIGS. 5–9 and 12–13, on Amberlite IRA-900 in the experiments shown in FIGS. 10 and 11, on aluminium monostearate in FIG. 14, on Amberlite XAD-16 in FIG. 15 and on Amberlite XAD-7 in FIG. 16. In all cases where lipase was modified by surfactant, the surfactant used for this treatment was sorbitan monostearate, except for the experiment shown in FIG. 13, where the surfactant was sorbitan tristearate.

Example 9

Covalent Binding of Modified and Non-modified Lipases to Eupergit

Lipases were covalently bound to Eupergit according to the manufacturer's specification. The covalent binding was carried out the two procedures described above.

TABLE X

| Enzyme form | Conversion (%) |
|---|---|
| Lilipase A10-FG | |
| Crude Lilipase A10FG | 2 |
| Lilipase on Eupergit | 4 |
| Lilipase on Eupergit + SMS | 19 |
| Lilipase on Eupergit + SMS after 48 h | 26 |
| Lipase LP | |
| Crude lipase LP | 1 |
| Lipase LP on Eupergit | 2 |
| Lipase LP on Eupergit + SMS | 14 |
| Lipase LP on Eupergit + SMS after 48 h | 18 |
| Lipase PS | |
| Crude lipase PS | 1 |
| Lipase PS on Eupergit | 2 |
| Lipase PS on Eupergit + SMS | 8 |
| Lipase PS on Eupergit + SMS after 48 h | 12 |

It can be seen from Table X that different lipases show different inter-esterification activity when are treated similarly. This result is ascribed to the different sources of the lipases used. All crude lipases showed very low inter-esterification activity under the described conditions while their activity has slightly increased when they were covalently immobilized on Eupergit. It is interesting to notice that when lipases were coated with a surfactant their inter-esterification activity has significantly increased. The highest conversion of tripalmitin to its inter-esterification products with 1,3-positional specificity that was achieved after 2 h reaction, was when the lipases were first covalently immobilized on Eupergit and then coated with surfactant. Lilipase A10-FG coated with the surfactant and immobilized on Eupergit yielded the highest inter-esterification activity within the three lipases tested in this respect (Table X).

Example 10

Effect of Binders on the Enzyme Activity

As previously mentioned, different binders have been used for the granulation of the modified-immobilized lipases. Table XI shows the average conversion of olive oil to its wax esters in the first and second runs, using different binders for granulating Lilipase A10-FG modified with sorbitan monostearate and immobilized on Celite. The percentage of all binders was 2% dry weight of the granules. In these experiments, the granulated enzyme was packed in a column and used in 10 runs.

The average conversion of olive oil to its wax esters in the first and second runs using Lilipase A 10FG modified with sorbitan monostearate and immobilized on Celite and then granulated with different binders (2%). Reaction conditions: 100 ml of n-Hexane containing 2 g olive oil and 2 g cetyl alcohol recirculated over an immobilized enzyme packed-bed at a circulation rate of 2.5 ml/min and at 40° C. Column dimensions: 12 cm long, 0.75 cm i.d.

TABLE XI

| Binder | Conversion (%) |
|---|---|
| Starch | 92 |
| Ethyl cellulose | 44.6 |
| Methyl cellulose | 38.1 |
| Agarose | 16.8 |
| Gelatin | Inactive |
| Polyvinylpyrrollodone | Inactive |
| Gum Arabic | 49.1 |
| Gum Xan | 33.2 |
| Gum Karaya | 49.5 |
| Gum Tragacanth | 20.1 |
| Gum Locas | 33.6 |

From the above table it may be concluded that starch, Gum Arabic and Gum Karaya are the most effective binders of those tested in this study, that yielded active biocatalysts.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A lipase preparation comprising an insoluble matrix and a surfactant-coated lipase complex immobilized onto said insoluble matrix, wherein said surfactant is a fatty acid polyol ester.

2. The lipase preparation of claim 1, wherein the surfactant-coated lipase complex is covalently, ionically or physically bound to the insoluble matrix.

3. The lipase preparation of claim 1, wherein the insoluble matrix is selected from the group consisting of an inorganic insoluble matrix and an organic insoluble matrix.

4. The lipase preparation of claim 3, wherein the inorganic insoluble matrix is selected from the group consisting of alumina, diatomaceous earth, Celite, calcium carbonate, calcium sulfate, silica gel and charcoal.

5. The lipase preparation of claim 3, wherein the organic insoluble matrix is selected from the group consisting of ion-exchange resin, Eupergit, ethylsulfoxycellulose and aluminum stearate.

6. The lipase preparation of claim 1, wherein the content of the lipase is 2–20 weight percent of the surfactant-coated lipase complex.

7. The lipase preparation of claim 1, wherein the content of the lipase is 0.01–1.0 weight percent of the preparation.

8. The lipase preparation of claim 1, wherein a fatty acid moiety in said fatty acid polyol ester is selected from the group consisting of monolaurate, monomyristate, monopalmitate, monostearate, dilaurate, dimyristate, dipalmitate, distearate, trilaurate, trimyristate, tripalmitate and tristearate.

9. The lipase preparation of claim 1, wherein said fatty acid polyol ester includes a sugar moiety.

10. The lipase preparation of claim 9, wherein the sugar is selected from the group consisting of sorbitol, sucrose, glucose and lactose.

11. The lipase preparation of claim 1, wherein the lipase is derived from a microorganism or a multicellular organism.

12. The lipase preparation of claim 1, wherein the lipase is selected from the group consisting of lipases derived from Burkholderia sp., *Candida antractica B*, *Candida rugosa*, Pseudomonas sp., *Candida antractica A*, Humicola sp.,

*Mucor miehei, Rhizopus javan, Pseudomonas fluor., Candida cylindrae, Aspergillus niger, Rhizopus oryzae, Mucor jauanicus,* Rhizopus sp., *Rhizopus japanicus, Candida antratica* and porcine pancreas.

13. The lipase preparation of claim 1 wherein the lipase preparation is provided in an organic solvent.

14. The lipase preparation of claim 13, wherein the organic solvent is selected from the group consisting of n-hexane, toluene, iso-octane, n-octane, benzene, cyclohexane and di-iso-propylether.

15. The lipase preparation of claim 1, wherein said preparation is in granulated form.

16. The lipase preparation of claim 1, wherein the insoluble matrix has been modified with a fatty acid derivative.

17. The lipase preparation according to claim 1, wherein said surfactant is sorbitan monostearate and said insoluble matrix is selected from Celite, hydrophobic silica and an ion exachanger Duolite A 568.

18. The lipase preparation of claim 17, wherein the surfactant in said surfactant-coated lipasae complex is selected from the group consisting of sorbitan monostearate (SMS), sorbitan tristearate, sorbitan trioloeate, sobitan monooleate, lecithin, stearic acid, poloxyethylene-8-stearate and sucrose esters.

19. The lipase preparation of claim 1, wherein said inorganic insoluble matrix is selected from the group consisting of alumina, silica, calcium carbonate and calcium sulfate.

20. The lipase preparation of claim 19 wherein the lipase preparation is in granulated form.

21. The lipase preparation of claim 17, wherein the inorganic insoluble matrix is Celite.

22. The lipase preparation of claim 21, wherein Celite is fatty acid treated or acid washed.

23. The lipase preparation of claim 5, wherein the ion-exchange resin is selected from the group consisting of Amberlite and Dowex.

24. A method comprising esterifying, inter-esterifying, or trans-esterifying oils or fats or alcoholysing triglycerols or fatty acids with a catalyst, the catalyst comprising the lipase preparation of claim 13.

25. The method of claim 24 wherein the catalyst has 1,3-positional specificity with respect to triacylglycerols.

26. The method of claim 24 wherein the esterifying, inter-esterifying, trans-esterifying or alcoholysing occurs with no added water.

27. A process for preparing structured triacylglycerols by esterification, acidolysis, trans-esterification, inter-esterification or alcoholysis between two substrates comprising contacting an insoluble matrix-immobilized surfactant-coated lipase complex according to claim 1 with said substrates.

28. The process of claim 27, wherein the matrix-immobilized surfactant-coated lipase complex is contacted with the substrates in the presence of an organic solvent.

29. The process of claim 27, wherein at least one of the substrates is selected from the group consisting of an oil, a fatty acid, a triacylglycerol and a fatty alcohol.

30. The process of claim 29, wherein the oil is selected from the group consisting of olive oil, soybean oil, peanut oil, fish oil, palm oil, cotton seeds oil, sunflower oil, Nigella sativa oil, canola oil and corn oil.

31. The process of claim 29, wherein the fatty acid is selected from the group consisting of medium and short-chain fatty acids and their ester derivatives.

32. The process of claim 29, wherein the fatty acid is selected from the group consisting of oleic acid, palmitic acid, linolic acid, linolenic acid, stearic acid, arachidonic acid, eicosapentaenoic acid, docosahexaenoic acid and their ester derivatives.

33. The process of claim 27, which is carried out in a tank reactor or in a fixed-bed reactor.

34. A method of preparing an insoluble matrix-immobilized surfactant-coated lipase complex comprising, in any desired order, the steps of:

(c) contacting a lipase in an aqueous medium with a surfactant consisting of a fatty acid polyol ester, at a concentration and temperature, and for a period of time sufficient to obtain a coating on said lipase; and (d) contacting said lipase in an aqueous medium, with an insoluble matrix, at a concentration, under conditions and for a period of time sufficient to obtain immobilization of said lipase on said matrix.

35. The method of claim 34, wherein said lipase is first contacted with the insoluble matrix, and thereafter with the surfactant.

36. The method of claim 34, wherein the lipase is first contacted with the surfactant, and thereafter with the insoluble matrix.

37. The method of claim 34, further comprising the step of:

(c) separating the matrix-immobilized surfactant-coated lipase complex from the aqueous solution in which it was formed.

38. The method of claim 37, further comprising the step of:

(d) drying the matrix-immobilized surfactant-coated lipase complex.

39. The method of claim 38, wherein drying is effected by freeze drying.

40. The method of claim 38, wherein the matrix-immobilized surfactant-coated lipase complex is dried to a water content of less than 100 parts per million by weight.

41. The method of claim 34, wherein the aqueous solution is a buffered aqueous solution.

42. The method of claim 34, wherein the lipase and surfactant are contacted in the aqueous medium by:

(i) dissolving said surfactant in an organic solvent for obtaining a dissolved surfactant solution; and (ii) mixing said lipase and said dissolved surfactant solution in said aqueous medium.

43. The method of claim 34, further comprising sonicating the aqueous solution.

44. The method of claim 34, a fatty acid moiety in said fatty acid polyol ester is selected from the group consisting of monolaurate, monomyristate, monopalmitate, monostearate, dilaurate, dimyristate, dipalmitate, distearate, trilaurate, trimyristate, tripalmitate and tristearate.

45. The method of claim 34, wherein said surfactant includes a sugar moiety.

46. The method of claim 45, wherein the sugar is selected from the group consisting of sorbitol, sucrose, glucose and lactose.

47. The method of claim 34, wherein the lipase is derived from an organism.

48. The method of claim 47, wherein the lipase is derived from a multicellular microorganism.

49. The method of claim 47, wherein the lipase is selected from the group consisting of lipases derived from Burkholderia sp., *Candida antractica B, Candida rugosa,* Pseudomonas sp., *Candida antractica A,* Humicola sp., *Mucor miehei, Rhizopus javan, Pseudomonas fluor., Candida cylindrae, Aspergillus niger, Rhizopus oryzae, Mucor javanicus,*

Rhizopus sp., *Rhizopus japanicus, Candida antratica* and *porcine pancreas*.

50. The method of claim 34, wherein the insoluble matrix is an inorganic insoluble matrix or an organic insoluble matrix.

51. The method of claim 50 wherein the insoluble matrix is an inorganic matrix selected from the group consisting of alumina, diatomaceous earth, Celite, calcium carbonate, calcium sulfate, silica-gel. charcoal, and fatty acid derivative-treated Celite.

52. The method of claim 50 wherein the insoluble matrix is an organic matrix selected from the group consisting of ion-exchange resin, Eupergit, ethylsulfoxycellulose and aluminum stearate.

* * * * *

UNITED STATES PATENT AND TRADEMARK OFFICE
CERTIFICATE OF CORRECTION

PATENT NO. : 6,605,452 B1
DATED : August 12, 2002
INVENTOR(S) : Sobhi Basheer et al.

Page 1 of 1

It is certified that error appears in the above-identified patent and that said Letters Patent is hereby corrected as shown below:

<u>Column 2,</u>
Line 26, "-3" has been removed;

<u>Column 4,</u>
Line 7, "inorganic" has been removed;
Line 50, "jaanicus" has been replaced with -- japonicus --;

<u>Column 6,</u>
Line 7, "eater" has been replaced with -- ester --;

<u>Column 9,</u>
Line 38, "inorganic" has been removed;

<u>Column 10,</u>
Line 5, "jaanicus" has been replaced with -- japonicus --;
Line 18, -- . -- has been added before "The method";

<u>Column 65,</u>
Line 65, -- , -- has been added after "Fish oil".

Signed and Sealed this

Third Day of February, 2004

JON W. DUDAS
*Acting Director of the United States Patent and Trademark Office*